US009734689B2

(12) United States Patent
Hyde et al.

(10) Patent No.: US 9,734,689 B2
(45) Date of Patent: *Aug. 15, 2017

(54) SYSTEMS WITH INTERACTIVE MANAGEMENT OF ENVIRONMENTAL OBJECTS RELATIVE TO HUMAN APPENDAGES

(71) Applicant: Elwha LLC, Bellevue, WA (US)

(72) Inventors: Roderick A. Hyde, Redmond, WA (US); Jordin T. Kare, San Jose, CA (US); Eric C. Leuthardt, St. Louis, MO (US); Mark A. Malamud, Seattle, WA (US); Tony S. Pan, Bellevue, WA (US); Elizabeth A. Sweeney, Seattle, WA (US); Clarence T. Tegreene, Mercer Island, WA (US); Charles Whitmer, North Bend, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/843,696

(22) Filed: Sep. 2, 2015

(65) Prior Publication Data

US 2017/0061764 A1   Mar. 2, 2017

(51) Int. Cl.
*G08B 21/04* (2006.01)
*G06K 7/10* (2006.01)

(52) U.S. Cl.
CPC ..... *G08B 21/0438* (2013.01); *G06K 7/10366* (2013.01)

(58) Field of Classification Search
CPC ........... G06K 7/10138; G06K 7/10128; G06K 7/10148; G06K 7/10158; G06K 7/10159;
(Continued)

(56) References Cited

U.S. PATENT DOCUMENTS 5,336,983 A   8/1994   Watanabe
5,784,238 A   7/1998   Nering et al.
(Continued)

OTHER PUBLICATIONS

Axisa, F., Brosteaux, D., De Leersnyder, E., Bossuyt, F., Vanfleteren, J., Hermans, B., Puers, R.; Biomedical Stretchable Systems Using Mid Based Stretchable Electronics Technology; Proceedings of the 29th Annual International Conference on the IEEE EMBS Cite International, Lyon, France; Aug. 23-26, 2007; pp. 5687-5690.

(Continued)

*Primary Examiner* — Van Trieu
(74) *Attorney, Agent, or Firm* — Daniel J. Honz; Advent, LLP

(57) ABSTRACT

Systems are described for analyzing an environment. A system embodiment includes, but is not limited to, a tag and a reader pair, the tag and the reader configured for individual positioning proximate a human appendage and an environmental object, wherein the reader is configured to identify the tag; a substrate configured to conform to the human appendage, the substrate coupled to at least one of the tag or the reader, the other of the tag or the reader configured to be coupled to the environmental object; a processor operably coupled to the reader and configured to receive one or more output signals from the reader, the one or more output signals corresponding to a threshold associated with the tag or the reader; and an output reporter operably coupled to the processor and configured to generate one or more communication signals responsive to instruction by the processor.

19 Claims, 18 Drawing Sheets

(58) Field of Classification Search
CPC ........... G06K 7/10366; G06K 7/10376; G06K 7/10386; G06K 7/10396; G06K 7/10405; G08B 1/00; G08B 21/22; G08B 21/245; G08B 21/04; G08B 21/0438; G06Q 50/22; G07K 7/10

See application file for complete search history.

(56) References Cited

U.S. PATENT DOCUMENTS

| | | | |
|---|---|---|---|
| 6,894,509 | B2 | 5/2005 | Johnson et al. |
| 7,132,944 | B1* | 11/2006 | Kron ............... G08B 21/0288 340/572.1 |
| 8,292,830 | B2 | 10/2012 | Bertocci |
| 2002/0067660 | A1 | 6/2002 | Bokhour |
| 2007/0159332 | A1* | 7/2007 | Koblasz .............. G06F 19/3456 340/572.1 |
| 2008/0146968 | A1 | 6/2008 | Hanawaka et al. |
| 2010/0271187 | A1 | 10/2010 | Uysal et al. |
| 2010/0324455 | A1 | 12/2010 | Rangel et al. |
| 2012/0075464 | A1 | 3/2012 | Derenne et al. |
| 2012/0165759 | A1 | 6/2012 | Rogers et al. |
| 2013/0041235 | A1 | 2/2013 | Rogers et al. |
| 2013/0253818 | A1 | 9/2013 | Sanders et al. |
| 2013/0304401 | A1 | 11/2013 | Tubaro et al. |
| 2013/0321168 | A1 | 12/2013 | Mahony et al. |
| 2014/0297371 | A1* | 10/2014 | Colburn ............... G06F 19/327 705/7.38 |
| 2015/0077257 | A1* | 3/2015 | Pokrajac ............... G08B 13/06 340/572.8 |
| 2015/0220762 | A1 | 8/2015 | Jiang et al. |
| 2015/0254964 | A1* | 9/2015 | Raichman ............ G08B 21/245 340/573.1 |

OTHER PUBLICATIONS

Kim, D. et al., Epidermal Electronics, Science, vol. 333 ,838-843 (2011), DOI: 10.1126/science.1206157.

Rojahn, Susan Young; "An Activity Tracker for Seniors;" http://www.technologyreview.com/news/525016/an-activity-tracker-for-seniors/?utm_campaign=newsletters&utm_source=newsletter-daily-all&utm_medium=email&utm_content=20140228; Feb. 27, 2014.

Salvatore, G.A. et al., Wafer-scale design of lightweight and transparent electronics that wraps around hairs, Nature Communications, 5:2982 (2014) | DOI: 10.1038/ncomms3982.

Sandhana, Lakshmi; "Siemen's smart C-Walker guides the cognitively impaired"; http://www.gizmag.com/c-walker-guides-cognitively-impaired/30369/; Jan. 8, 2014; ).

Torpy, J.M., Peripheral Neuropathy; The Journal of American Medical Association; Apr. 21, 2010; vol. 303, No. 15; p. 1.

Wang, C. et al., A Flexible Proximity Sensor Fully Fabricated by Inkjet Printing, Sensors, 10(5) 2010; DOI: 10.3390/s100505054.

Xu, S. et al, Soft Microfluidic Assemblies of Sensors, Circuits, and Radios for the Skin, Science, vol. 344, 70-74 (2014).

Yeo, W. et al., Multifunctional Epidermal Electronics Printed Directly Onto the Skin, Advanced Materials vol. 25(20), 2773-2778 (2013).

Ying, M. et al., Silicon nanomembranes for fingertip electronics, Nanotechnology, vol. 23, No. 34, 1-7 (2012).

PCT International Search Report; International App. No. PCT/US2016/049595; Nov. 11, 2016; pp. 1-3.

* cited by examiner

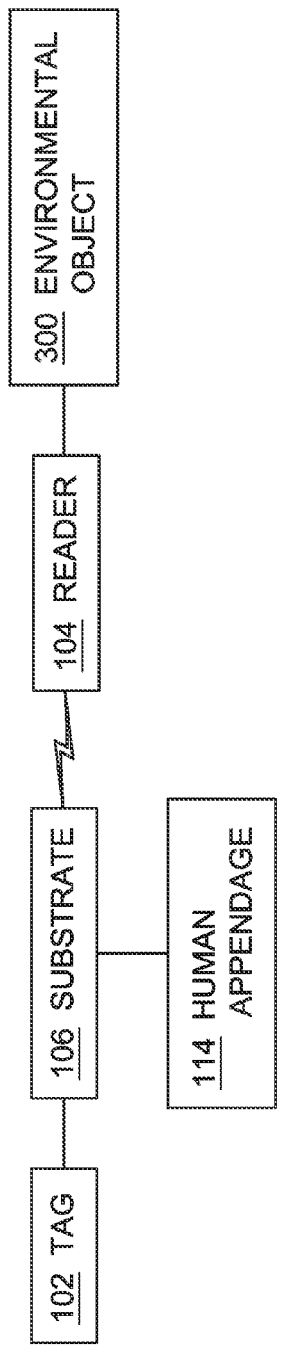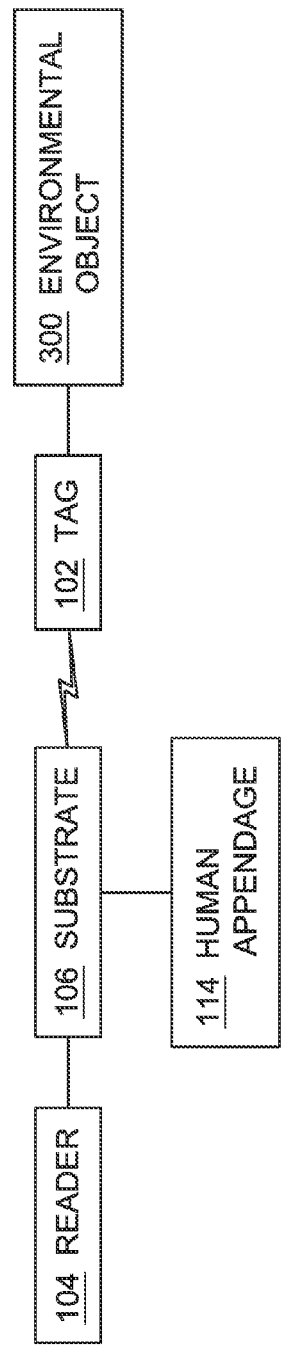
FIG. 3A
FIG. 3B

SYSTEMS WITH INTERACTIVE MANAGEMENT OF ENVIRONMENTAL OBJECTS RELATIVE TO HUMAN APPENDAGES

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)).

PRIORITY APPLICATIONS

None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In an aspect, a system includes, but is not limited to, a tag and a reader pair, the tag and the reader configured for individual positioning proximate a human appendage and an environmental object, wherein the reader is configured to identify the tag; a substrate configured to conform to the human appendage, the substrate coupled to at least one of the tag or the reader, the other of the tag or the reader configured to be coupled to the environmental object; a processor operably coupled to the reader and configured to receive one or more output signals from the reader, the one or more output signals corresponding to a threshold associated with the tag or the reader; and an output reporter operably coupled to the processor and configured to generate one or more communication signals responsive to instruction by the processor.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 3A is a schematic of an embodiment of a system such as shown in FIG. 1.

FIG. 3B is a schematic of an embodiment of a system such as shown in FIG. 1.

DETAILED DESCRIPTION

Figure 1:
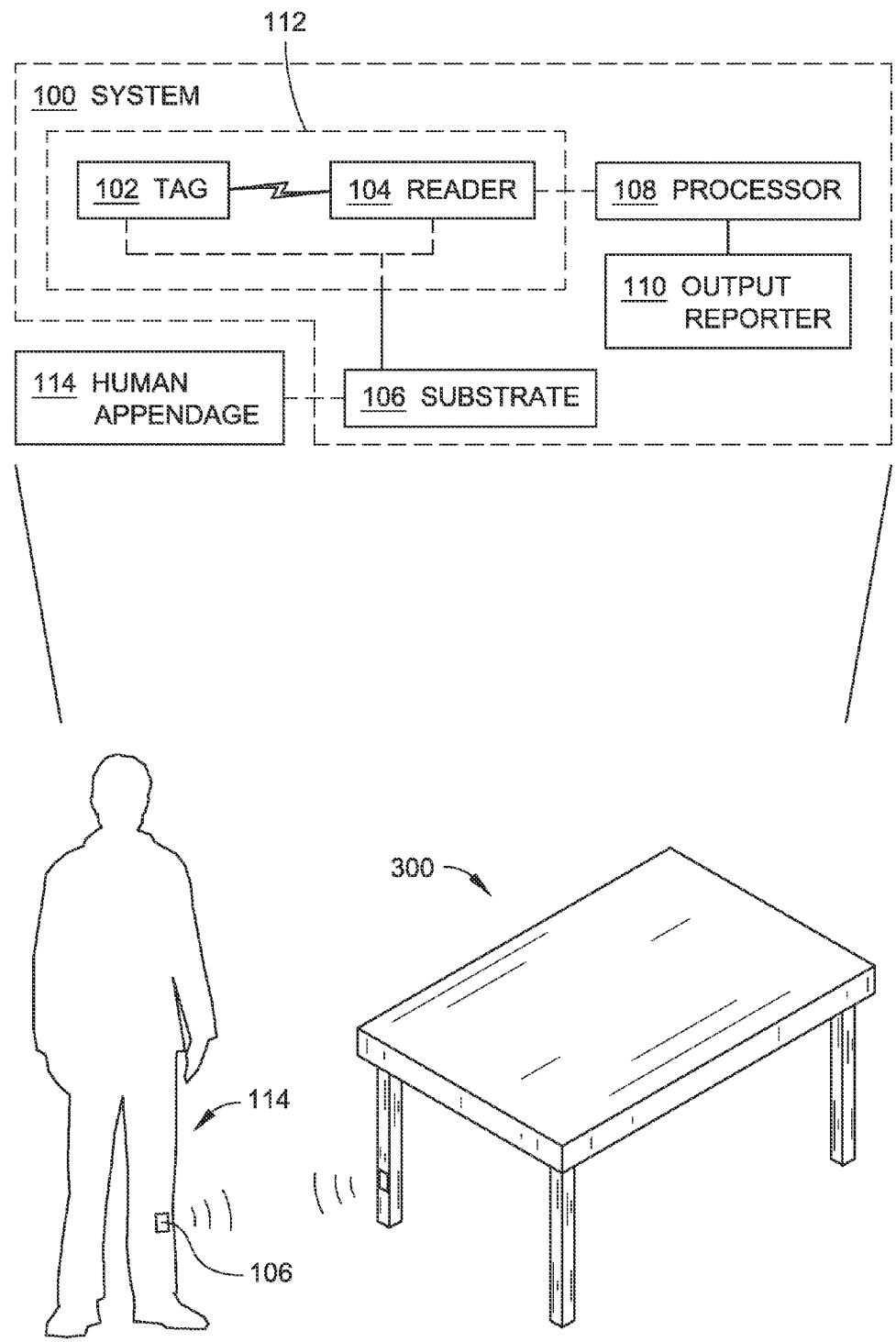
FIG. 1 is a schematic of a system with interactive management of environmental objects relative to human appendages.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Systems are described for monitoring environmental conditions around human appendages to aid in preventing damage (tissue damage, nerve damage, or the like) associated with physical impact between the appendages and environmental objects. Such systems can monitor the environment in proximity to body portions of an individual to identify potential hazards for collision with the body portion, such as environmental objects in proximity to the body portion. Such systems can determine what environmental objects pose a risk for impact, which can be based on frequency of impact or repeated risks of impact. Such systems can provide locations associated with impending impacts and warn individuals of impending impact. Such systems can analyze proximity information for a particular period of time and provide recommendations configured to reduce the likelihood of impact with an environmental object or reduce a severity of impact with the environmental object. For example, the systems can be associated with an individual afflicted with neuropathy, an individual in a medical facility, an individual with visual impairments that reduce their ability to acknowledge environmental conditions while physically maneuvering about the environment, an individual that negotiates dark environments (e.g., wakes and moves about at night), or so forth. Individuals afflicted with neuropathy (e.g., peripheral neuropathy) may have reduced capabilities to detect when a body portion comes in contact with another object or a surface due to an impairment of sensation, movement, or other normal body functions. Neuropathy can result from a disease, such as diabetes or immune system diseases, from interactions with various medications or medical treatments (such as chemotherapy), from inherited characteristics, from vitamin deficiency, from traumatic injury, from excessive alcohol usage, from infections (e.g., human immunodeficiency virus (HIV)), or other conditions and sources. In embodiments, the systems and devices described herein can monitor an environment to determine whether an object in the environment poses a risk for impact with human appendages, can analyze information associated with impacts with an environmental object or near impacts with an environmental object (e.g., when an appendage and the environmental object come within a distance threshold), can provide recommendations configured to reduce the likelihood of impact with an environmental object or reduce a severity of impact with the environmental object, or so forth. The systems/devices can be positioned on the appendages, near the appendages, or remote from the appendages. The systems/devices can report information including, but not limited to, information corresponding to a threshold associated with the appendage and the environmental object. The information corresponding to the threshold associated with the appendage and the environmental object can include, but is not limited to, information associated with a threshold distance between the appendage and the environmental object being met or exceeded, information associated with a frequency of impacts between the appendage and the environmental object, information associated with a frequency of near impacts, information associated with a warning of impact, information associated with a recommendation configured to reduce the likelihood of impact with an environmental object or reduce a severity of impact with the environmental object, or so forth.

In embodiments, the systems and devices described herein employ a tag and a reader pair, where the tag and the reader are configured for individual positioning proximate a human appendage and an environmental object. The tag can include, but is not limited to, an RFID tag, a magnetic material, or an optical label. The reader can be operably coupled with a processor configured to receive one or more output signals from the reader. The processor can be configured to make one or more determinations based on the one or more output signals and to instruct an output reporter to provide information associated with the human appendage and/or the environmental object. The information can include, but is not limited to, recommendations configured to reduce the likelihood of impact with the environmental object, reduce a severity of impact with the environmental object, or so forth.

In embodiments, the systems and devices described herein employ a plurality of tags, where at least one tag is coupled to a substrate configured to conform to a human appendage and where at least one other tag is configured to be coupled to an environmental object. The tags can include, but are not limited to, RFID tags, magnetic materials, or optical labels. The systems and devices described herein can also employ a remote reader positioned remotely from the plurality of tags, where the remote reader can be operably coupled to a processor configured to receive one or more output signals from the remote reader. The processor can be configured to make one or more determinations based on the one or more output signals and to instruct an output reporter to provide information associated with the human appendage and/or the environmental object. The information can include, but is not limited to, recommendations configured to reduce the likelihood of impact with the environmental object, reduce a severity of impact with the environmental object, or so forth.

In embodiments, the systems and devices described herein employ a plurality of sensors, where each sensor of the plurality of sensors is configured for positioning proximate a respective environmental object of a plurality of environmental objects. The sensors can include, but are not limited to, proximity sensors, pressure sensor, or accelerometers. The systems and devices described herein can also employ a remote device positioned remotely from the plurality of sensors, where the remote device can be operably coupled to a processor configured to receive one or more output signals from the remote device. The processor can be configured to make one or more determinations based on the one or more output signals and to instruct an output reporter to provide information associated with the human appendage and/or the environmental object. The information can include, but is not limited to, recommendations configured to reduce the likelihood of impact with the environmental object, reduce a severity of impact with the environmental object, or so forth.

In embodiments, the systems and devices described herein employ an output reporter configured to generate one or more communication signals responsive to instruction by a processor. The output reporter can convey information via the one or more communication signals, including but not limited to, an auditory indication of the information, a visual indication of the information, or a tactile indication of the information.

Figure 2:
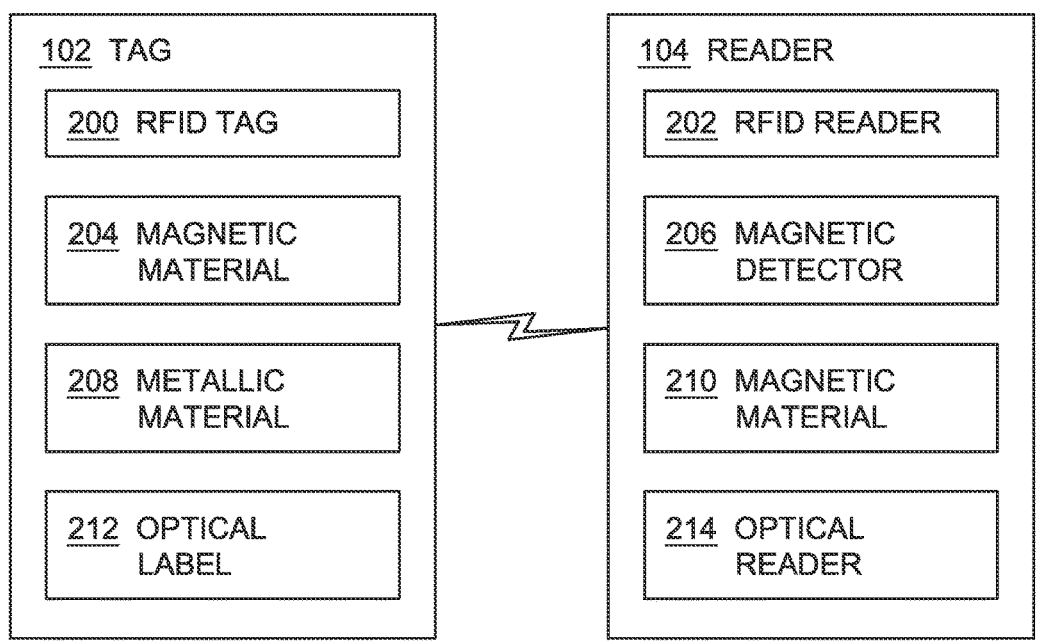
FIG. 2 is a schematic of an embodiment of a system such as shown in FIG. 1.

In embodiments, shown in FIG. 1, a system (or device) 100 is configured to monitor an environment through which an individual can move, where the system can identify environmental objects in proximity to an appendage of the individual to aid in preventing damage to one or more of the individual or the environmental object associated with physical impact between the environmental object and the appendage. The system 100 includes a tag 102, a reader 104, a substrate 106, a processor 108, and an output reporter 110. The tag 102 and the reader 104 form a tag and a reader pair 112 where the reader 104 is configured to identify the tag 102 through one or more identification protocols. For example, the tag 102 can include, but is not limited to, a radio frequency identification (RFID) tag, where the reader 104 can include, but is not limited to, an RFID reader. FIG. 2 shows an embodiment where the tag 102 includes an RFID tag 200 and where the reader 104 includes an RFID reader 202 configured to at least one of identify or detect the RFID tag 200. The tag 102 can also include, but is not limited to, a magnetic material (e.g., a diamagnetic material, a paramagnetic material, a ferromagnetic material, etc.), where the reader 104 can include, but is not limited to, a magnetic detector (e.g., a magnetic field detector, a magnetometer, etc.). FIG. 2 shows an embodiment where the tag 102 includes a magnetic material 204 and where the reader 104 includes a magnetic detector 206 configured to at least one of identify or detect the magnetic material 204. The tag 102 can also include, but is not limited to, a metallic material, where the reader 104 can include, but is not limited to a magnetic material configured to at least one of identify or detect the metallic material. FIG. 2 shows an embodiment where the tag 102 includes a metallic material 208 and where the reader 104 includes a metallic material 210 configured to at least one of identify or detect the metallic material 208. The tag 102 can also include, but is not limited to an optical label (e.g., a bar code, a matrix barcode (e.g. QR code), etc.), where the reader 104 can include, but is not limited to an optical reader (e.g., a camera, an imaging device, a scanner, etc.). FIG. 2 shows an embodiment where the tag 102 includes an optical label 212 and where the reader 104 includes an optical reader 214 configured to at least one of identify or detect the optical label 212.

The substrate 106 is configured to conform to a human appendage 114. For example, the substrate 106 can comprise a deformable (e.g., conformable, flexible, stretchable, etc.) material configured to interface with, and conform to, the human appendage 114. The deformable and conformable nature of the substrate 106 facilitates interaction/interfacing with the human appendage 114, which includes a generally low-modulus and deformable natural skin surface. The substrate 106 can with associated with one or more of a shoe, a sock, a finger cot, a wrap, a glove, a ring, or a bracelet such that the substrate 106 can conform to respective human appendages. For example, the human appendage 114 can include, but is not limited to, an arm, an elbow, a wrist, a hand, a finger, a leg, a knee, an ankle, a foot, or a toe. In embodiments, the substrate 106 can include one or more of a stretchable/flexible fabric, an elastomeric polymer, a hydrocolloid film, a nanomembrane (e.g., silicon nanomembrane), or other deformable/conformable material. The substrate 106 can be positioned in proximity with the skin surface according to various mechanisms including, but not limited to, affixed to the skin via an adhesive material, held in place by an external pressure, such as pressure provided by a material wrapped around or about a body portion (e.g., a fabric, a garment, a bandage, etc.), or so forth.

The substrate 106 is configured to be coupled to at least one member of the tag and reader pair 112 to support the at least one member of the tag and reader pair 112 relative to the human appendage 114. When the substrate 106 is applied to the human appendage 114, the at least one member of the tag and reader pair 112 can move with the human appendage 114, travel through the environment with the human appendage 114, or so forth due to the conforming of the substrate 106 to the human appendage 114. In embodiments, the substrate 106 is configured to couple to the tag 102 of the tag and reader pair 112. For example, as shown in FIG. 3A, the substrate 106 is coupled to the tag 102, whereas the reader 104 is associated with an environmental object 300 located within an environment. In general, the environmental object 300 is a physical object present within the environment that can pose a hazard for impact with an individual. The environmental object can be a permanent or a semi-permanent feature of the environment, or can be a positionable (e.g., emplaceable) object in the environment. In an embodiment, an environmental object can be, for example, a substantially stationary object that is meant to take up designated space in the environment. An environmental object can be, for example, an immovable object or a permanent object in the environment, such as a fixture in a room, a wall, a counter, a fireplace, a kitchen appliance and the like. An environmental object can be, for example, an object set in a semi-permanent position, for example a large piece of furniture such as a desk or sofa. An environmental object can be, for example, a positionable or emplaceable object that has a designated place and position in the environment, the designated place and position being purposefully altered at will. Examples of positionable or emplaceable pieces found in a room would be a table, a coffee table, a chair, and the like. In embodiments, the environmental object 300 can include, but is not limited to, a furniture item, a chair, a table, a sofa, a desk, a wall, a door, a hanging or suspended object, or portions thereof. For example, the environmental object 300 can include a portion of a furniture item, such as a furniture leg, an edge of a furniture item (e.g., an edge of a coffee table, an edge of a desk, etc.), or the like that can pose a hazard for impact with an individual as the individual moves through the environment. As another example, the environmental object 300 can include a portion of a desk and/or an item supported by the desk, such as a keyboard, a container, an edge of the desk, or the like that can pose a hazard for impact with a portion of the individual, such as the individual's hands or fingers, particularly where the individual is affected by neuropathy or other condition affecting nervous system functionality. As another example, the environmental object 300 can include a wall, a door, or portions thereof, such as a door frame, a doorjamb, a door threshold, or the like. In certain embodiments, the environment in which the environmental object (s) reside might be a smaller area. For example, when the appendage 114 is a finger of a person suffering from neuropathy in the hands, the environment might be a desktop. Environmental objects on a desktop can include immovable objects such as edges, keyboard supports and the like. Additionally, environmental objects on a desktop can include substantially stationary objects such as a monitor, printer, etc., while positionable objects can include such items as a lamp, a storage container (e.g., pen holder or coffee cup), a phone, etc.

The reader 104 can couple to the environmental object 300 such that the reader 104 is at least partially supported by the environmental object 300. For example, the reader 104 can couple to the environmental object 300 via an adhesive material, via an external pressure (e.g., such as pressure provided by a material wrapped around or about the environmental object 300), or so forth. The reader 104 is configured to one or more of communicate with or identify the tag 102, and can generate one or more output signals responsive to one or more of communications with or identification of the tag 102. When the tag 102 is coupled to the substrate 106 (e.g., as shown in an embodiment in FIG. 3A), the tag 102 can move through the environment during movement of the human appendage 114 through the environment. Such movement can include, but is not limited to, movement of a foot during walking across a floor of an environment, movement of a hand across a table surface, movement of fingers across a keyboard surface, or so forth. The reader 104 can detect changes in the distance or proximity between the reader 104 and the tag 102 as the tag 102 moves through the environment. Such detected changes and other information associated with the distance or proximity between the reader 104 and the tag 102 can processed by the processor 108 and reported by the output reporter 110 as described further herein.

In embodiments, the substrate 106 is configured to couple to the reader 104 of the tag and reader pair 112. For example, as shown in FIG. 3B, the substrate 106 is coupled to the reader 104, whereas the tag 102 is associated with the environmental object 300 located within an environment. The tag 102 can couple to the environmental object 300 such that the tag 102 is at least partially supported by the environmental object 300. For example, the tag 102 can couple to the environmental object 300 via an adhesive material, via an external pressure (e.g., such as pressure provided by a material wrapped around or about the environmental object 300), or so forth. The reader 104 is configured to one or more of communicate with or identify the tag 102, and can generate one or more output signals responsive to one or more of communications with or identification of the tag 102. When reader 104 is coupled to the substrate 106 (e.g., as shown in an embodiment in FIG. 3B), the reader 104 can move through the environment during movement of the human appendage 114 through the environment. Such movement can include, but is not limited to, movement of a foot during walking across a floor of an environment, movement of a hand across a table surface, movement of fingers across a keyboard surface, or so forth. The reader 104 can detect changes in the distance or proximity between the reader 104 and the tag 102 as the reader 104 moves through the environment. Such detected changes and other information associated with the distance or proximity between the reader 104 and the tag 102 can processed by the processor 108 and reported by the output reporter 110 as described further herein.

The processor 108 is operably coupled to the reader 104 and is configured to receive one or more output signals from the reader 104. The processor 108 and the reader 104 can communicate via wired or wireless communication protocols such that the processor 108 receives the one or more output signals from the reader 104. For example, the processor 108 can be positioned remotely from the reader 104, positioned adjacent to the reader 104, coupled to the reader 104 and/or the substrate 106, or the like. In general, the one or more output signals from the reader 104 correspond to information associated with one or more of the tag 102 or the reader 104. For example, the one or more output signals from the reader 104 correspond to a threshold associated with the tag 102 or the reader 104. In embodiments, the threshold associated with the tag 102 or the reader 104 is a distance threshold between the tag 102 and the reader 104, where the processor 108 can process the one or more output signals to make a determination regarding when the tag 102 and the reader 104 are at a distance that is less than the distance threshold. The distance threshold can correspond to a value indicative of an impending impact, or a near miss, such that when a distance between the tag 102 and the reader 104 is less than the threshold distance, the tag 102 and the reader 104 can be at risk for impact with each other. For example, in embodiments, the distance threshold is between about one-eighth inch and about ten feet, although other distance thresholds can be utilized which can depend on the configuration of the environment and the environmental object(s) 300. In embodiments, the threshold associated with the tag 102 or the reader 104 is a frequency threshold between the tag 102 and the reader 104. The frequency threshold can correspond to a frequency of occurrences associated with the tag 102 and the reader 104, such as a frequency of occurrence of impact between the tag 102 and the reader 104, a frequency of occurrence of near impact (e.g., a distance less than the threshold distance but not in contact) between the tag 102 and the reader 104, a frequency of occurrence of interaction between the tag 102 and the reader 104, a frequency of occurrence of identification by the reader 104 of the tag 102, a frequency of occurrence of detection by the reader 104 of the tag 102, or the like. The processor 108 can process the one or more output signals associated with the frequency threshold to make a determination pertaining to a frequency of occurrences between the tag 102 and the reader 104.

The processor 108 includes components to process the one or more output signals from the reader 104 and to provide instruction to the output reporter 110 to generate one or more communication signals associated with one or more of data associated with the one or more output signals or determinations made by the processor 108. For example, the processor 108 can include a microprocessor, a central processing unit (CPU), a digital signal processor (DSP), an application-specific integrated circuit (ASIC), a field programmable gate entry (FPGA), or the like, or any combinations thereof, and can include discrete digital or analog circuit elements or electronics, or combinations thereof. In one embodiment, the computing device includes one or more ASICs having a plurality of predefined logic components. In one embodiment, the computing device includes one or more FPGAs having a plurality of programmable logic commands.

Figure 4:
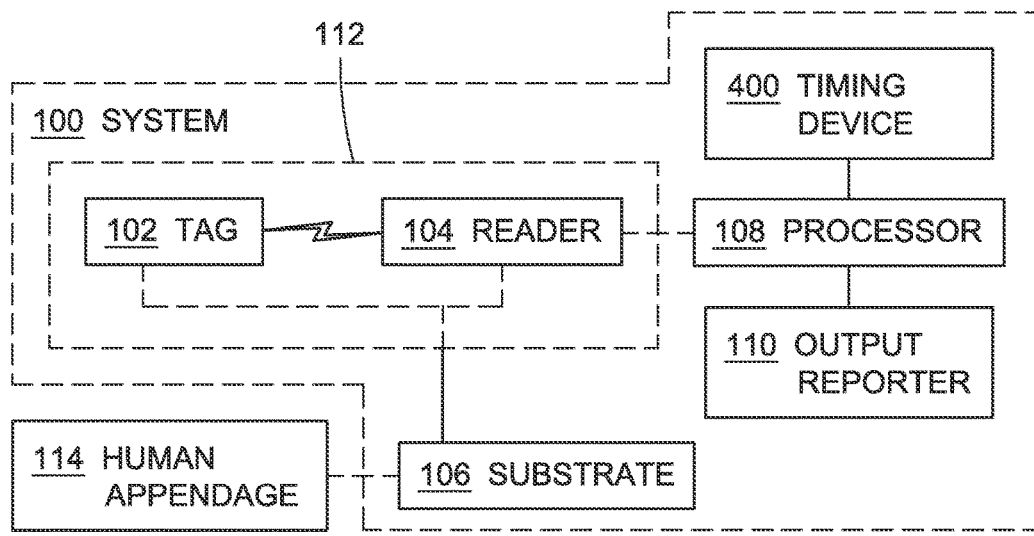
FIG. 4 is a schematic of an embodiment of a system such as shown in FIG. 1.

In embodiments, the processor 108 is configured to determine that an impact has occurred between the human appendage 114 and the environmental object 300 based on the one or more output signals from the reader 104. For example, an interaction or impact between the tag 102 and the reader 104 can be used as a proxy for determining an impact has occurred between the human appendage 114 and the environmental object 300. In embodiments, the processor 108 is configured to determine a time of the impact between the human appendage 114 and the environmental object 300 based on the one or more output signals from the reader 104. For example, as provided in FIG. 4, the system 100 can include a timing device 400 communicatively coupled with the processor 108 and configured to provide timing information or data to the processor 108, where such timing information can include, for example, a time at which the human appendage 114 and the environmental object 300 impact each other. The timing device 400 can include, but is not limited to a mechanical timing device, an electromechanical timing device, an electrical timing device, a programmable logic controller, a hardware timing device, or the like. In embodiments, the processor 108 is configured to determine a frequency of impacts between the human appendage 114 and the environmental object 300 based on the one or more output signals from the reader 104. The processor 108 can determine the frequency of impacts for an operation period of the system 100, for a specified period of time, for an average time span, or the like. In embodiments, the processor 108 can determine the time since a previous impact between the human appendage 114 and the environmental object 300 based on the one or more output signals from the reader 104.

In embodiments, the processor 108 is configured to determine when a distance between the human appendage 114 and the environmental object 300 is less than the threshold distance based on the one or more output signals from the reader 104. Such determination can provide an indication that the human appendage 114 and the environmental object 300 are within sufficient proximity to pose a threat for impact with one another, or missed impacting each other by a margin that is less than the threshold distance (e.g., a near impact). For example, an interaction or impact between the tag 102 and the reader 104 can be used as a proxy for determining that the human appendage 114 and the environmental object 300 are at a distance from each other that is less than the threshold distance. The threshold distance can be a predetermined value that corresponds to a safety consideration to prevent or mitigate impact between the human appendage 114 and the environmental object 300. In embodiments, the processor 108 is configured to determine a time corresponding to when the distance between the human appendage 114 and the environmental object 300 became less than the threshold distance based on the one or more output signals from the reader 104. The timing device 400 can be configured to provide a time at which the human appendage 114 and the environmental object 300 came within the threshold distance with respect to each other. For example, when the processor 108 determines that the human appendage 114 and the environmental object 300 are within the threshold distance with respect to each other, the processor 108 can refer to the timing device 400 to receive the current time from the timing device 400. In embodiments, the processor 108 is configured to determine a frequency of instances when the distance between the human appendage 114 and the environmental object 300 became less than the threshold distance based on the one or more output signals from the reader 104. The processor 108 can determine the frequency of such instances for an operation period of the system 100, for a specified period of time, for an average time span, or the like. In embodiments, the processor 108 can determine the time since a previous instance of when the human appendage 114 and the environmental object 300 came within the threshold distance with respect to each other based on the one or more output signals from the reader 104.

Figure 5:
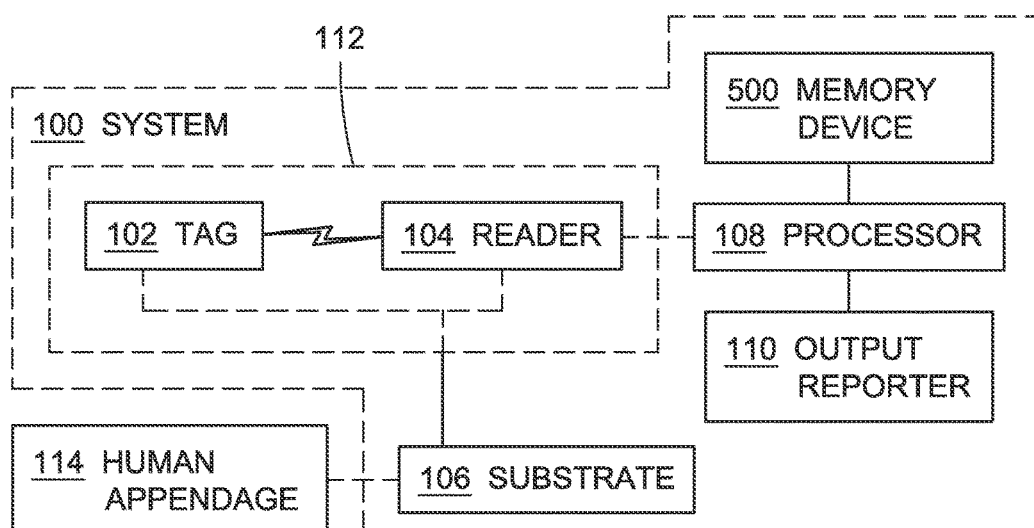
FIG. 5 is a schematic of an embodiment of a system such as shown in FIG. 1.

In embodiments (such as shown in FIG. 5), the system 100 includes a memory device 500 configured to store data associated with operation of the system 100, such as data associated with one or more of the tag 102 or the reader 104. The memory device 500 can include, but is not limited to, a computer memory device, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other medium which can be used to store the desired information maintained by the system 100 and which can be accessed by the processor 108, the output reporter 110, or other associated accessing device. In embodiments, the memory device 500 can store data associated with an impact or near impact between the human appendage 114 and the environmental object 300. The data associated with an impact between the human appendage 114 and the environmental object 300 can include, but is not limited to, a time of the impact between the human appendage 114 and the environmental object 300, or a frequency of occurrences of impact between the human appendage 114 and the environmental object 300. In embodiments, the memory device 500 can store data associated with when the distance between the human appendage 114 and the environmental object 300 is less than the threshold distance. The data associated with when the distance between the human appendage 114 and the environmental object 300 is less than the threshold distance can include, but is not limited to, data associated with when the distance between the human appendage 114 and the environmental object 300 is less than the threshold distance, or a frequency of instances of when the distance between the human appendage 114 and the environmental object 300 is less than the threshold distance.

Figure 6:
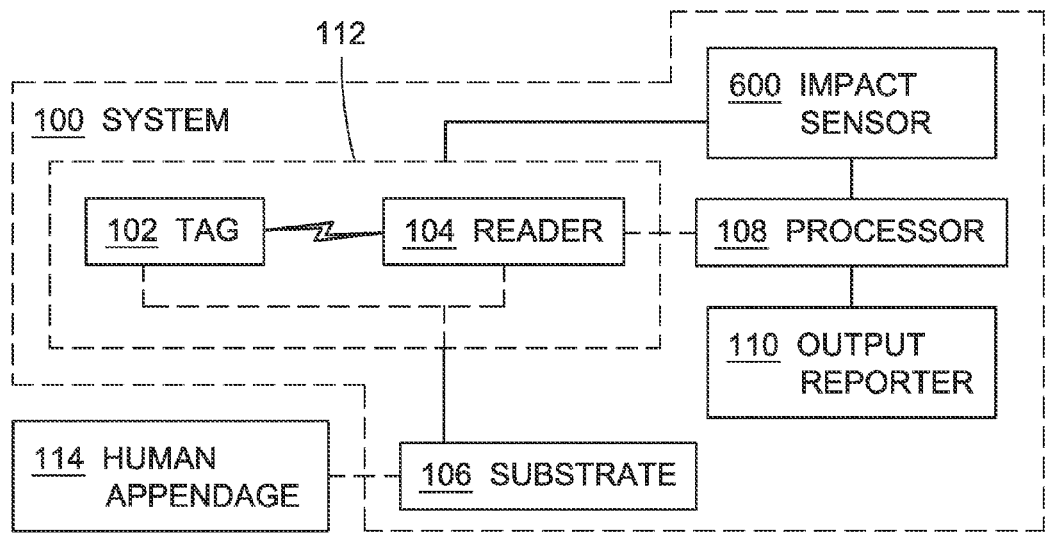
FIG. 6 is a schematic of an embodiment of a system such as shown in FIG. 1.

In embodiments (such as shown in FIG. 6), the system 100 includes an impact sensor 600 configured to provide one or more output signals corresponding to a detected impact or near impact associated with one or more of the tag 102 or the reader 104. The impact sensor 600 can include, but is not limited to, one or more of a proximity sensor, a pressure sensor, or an accelerometer. For example, the impact sensor 600 can include multiple (i.e., more than one) sensors of the proximity sensor, the pressure sensor, and the accelerometer, such as both of a proximity sensor and a pressure sensor, each of a proximity sensor, a pressure sensor, and an accelerometer, or so forth. The proximity sensor can include one or more of an optical proximity sensor, an acoustic proximity sensor, or an electromagnetic proximity sensor. The optical proximity sensor, the acoustic proximity sensor, and the electromagnetic proximity sensor can be configured to emit signals and detect reflected signals in accordance with their specific detection protocols. An optical proximity sensor can detect one or more optical signals (e.g., one or more optical electromagnetic signals) and generate one or more sense signals in response thereto. For example, an optical proximity sensor of the impact sensor 600 can be configured to detect and/or identify an environmental object 300 and/or a human appendage 114, and their proximity relative to components of the system 100 based on detected optical signals. The optical sensor can include, but is not limited to, a photodetector (e.g., to detect one or more electromagnetic signals reflected from a surface of an object), an imaging device (e.g., a camera to generate a visual image of one or more objects in proximity to components of the system 100), or the like. For example, an optical proximity sensor of the impact sensor 600 can be configured to emit a light signal and detect a reflected light signal, for example a reflected light signal that is reflected by an environmental object 300 and/or a human appendage 114. The acoustic proximity sensor can detect and/or identify objects and their proximity relative to components of the system 100 based on detected acoustic signals. For example, an acoustic proximity sensor of the impact sensor 600 can be configured to detect and/or identify an environmental object 300 and/or a human appendage 114, and their proximity relative to components of the system 100 based on detected acoustic signals. For example, an acoustic proximity sensor of the impact sensor 600 can be configured to emit an acoustic signal and detect a reflected signal, for example a reflected acoustic signal that is reflected by an environmental object 300 and/or a human appendage 114. The acoustic proximity sensor can include, but is not limited to, sensors configured to detect ultrasonic signals, radio-frequency signals, or the like. An electromagnetic proximity sensor can detect and/or identify objects and their proximity relative to components of the system 100 based on detected electromagnetic signals. For example, an electromagnetic proximity sensor of the impact sensor 600 can be configured to detect and/or identify an environmental object 300 and/or a human appendage 114, and their proximity relative to components of the system 100 based on detected electromagnetic signals. For example, an electromagnetic proximity sensor of the impact sensor 600 can be configured to emit an electromagnetic signal and detect a reflected electromagnetic signal, for example a reflected electromagnetic signal that is reflected by an environmental object 300 and/or a human appendage 114. The electromagnetic proximity sensor can include, for example, a bolometer or a thermal imaging device (e.g., to measure incident electromagnetic radiation of objects in proximity to components of the system 100). In embodiments, the impact sensor 600 includes a pressure sensor configured to sense a direct impact, such as an impact between the environmental object and the human appendage 114.

The processor 108 can be communicatively coupled with the impact sensor 600 to receive the one or more output signals from the impact sensor 600. In embodiments, the processor 108 is configured to determine that an impact has occurred between the human appendage 114 and the environmental object 300 based at least in part on the one or more output signals from the impact sensor 600. For example, the impact sensor 600 can be positioned on or in close proximity to one or more of the human appendage 114 or the environmental object 300, such as by associating the impact sensor 600 with one or more of the tag 102 or the reader 104. In embodiments, the processor 108 is configured to determine a time of the impact between the human appendage 114 and the environmental object 300 based on the one or more output signals from the impact sensor 600. For example, the timing device 400 (e.g., shown in FIG. 4) can be communicatively coupled with the processor 108, where the processor 108 can access a time from the timing device 400 when the one or more output signals from the impact sensor 600 provide an indication that an impact has occurred between the human appendage 114 and the environmental object 300. In embodiments, the processor 108 is configured to determine a frequency of impacts between the human appendage 114 and the environmental object 300 based on the one or more output signals from the impact sensor 600. The processor 108 can determine the frequency of impacts for an operation period of the system 100, for a specified period of time, for an average time span, or the like. In embodiments, the processor 108 can determine the time since a previous impact between the human appendage 114 and the environmental object 300 based on the one or more output signals from the impact sensor 600.

In embodiments, the processor 108 is configured to determine when a distance between the human appendage 114 and the environmental object 300 is less than the threshold distance based at least in part on the one or more output signals from the impact sensor 600. The threshold distance can be a predetermined value that corresponds to a safety consideration to prevent or mitigate impact between the human appendage 114 and the environmental object 300. In embodiments, the processor 108 is configured to determine a time corresponding to when the distance between the human appendage 114 and the environmental object 300 became less than the threshold distance based on the one or more output signals from the impact sensor 600. For example, the timing device 400 can be configured to provide a time at which the human appendage 114 and the environmental object 300 came within the threshold distance with respect to each other. In embodiments, the processor 108 is configured to determine a frequency of instances when the distance between the human appendage 114 and the environmental object 300 became less than the threshold distance based on the one or more output signals from the impact sensor 600. The processor 108 can determine the frequency of such instances for an operation period of the system 100, for a specified period of time, for an average time span, or the like. In embodiments, the processor 108 can determine the time since a previous instance of when the human appendage 114 and the environmental object 300 came within the threshold distance with respect to each other based on the one or more output signals from the impact sensor 600.

In embodiments, the memory device 500 can store data associated with an impact or near impact between the human appendage 114 and the environmental object 300, where a determination of the impact is based at least in part on the one or more output signals from the impact sensor 600. The data associated with an impact between the human appendage 114 and the environmental object 300 can include, but is not limited to, a time of the impact between the human appendage 114 and the environmental object 300, or a frequency of occurrences of impact between the human appendage 114 and the environmental object 300. In embodiments, the memory device 500 can store data associated with when the distance between the human appendage 114 and the environmental object 300 is less than the threshold distance, where a determination that the distance between the human appendage 114 and the environmental object 300 is less than the threshold distance is based at least in part on the impact sensor 600. The data associated with when the distance between the human appendage 114 and the environmental object 300 is less than the threshold distance can include, but is not limited to, data associated with when the distance between the human appendage 114 and the environmental object 300 is less than the threshold distance, or a frequency of instances of when the distance between the human appendage 114 and the environmental object 300 is less than the threshold distance.

In embodiments, the processor 108 is configured to determine that an impact has occurred between the human appendage 114 and the environmental object 300 based on the one or more output signals from the reader 104 and the one or more output signals from the impact sensor 600. For example, the reader 104 can provide data associated with the proximity of the tag 102 relative to the reader 104, which can provide an indication of when the human appendage 114 is close to or impacted with the environmental object 300. The impact sensor 600 can be positioned on or in close proximity to one or more of the human appendage 114 or the environmental object 300, such as by associating the impact sensor 600 with one or more of the tag 102 or the reader 104, and can provide data associated with impact to the human appendage 114 or the environmental object 300 depending on where the impact sensor 600 is located. For example, the impact sensor 600 can be associated with a tag 102 located on the environmental object 300 and can register an impact to the environmental object 300. The reader 104 can provide supplementary data to determine that the human appendage 114 caused the impact, such as when the reader 104 is coupled to the substrate 106 applied to the human appendage 114, where the reader 104 can identify the tag 102 via the tag and reader pair 112 relationship. In embodiments, the processor 108 is configured to determine a time of the impact between the human appendage 114 and the environmental object 300 based on the one or more output signals from the reader 104 and the one or more output signals from the impact sensor 600. For example, the timing device 400 (e.g., shown in FIG. 4) can be communicatively coupled with the processor 108, where the processor 108 can access a time from the timing device 400 when the one or more output signals from the impact sensor 600 provide an indication that an impact has occurred between the human appendage 114 and the environmental object 300. In embodiments, the processor 108 is configured to determine a frequency of impacts between the human appendage 114 and the environmental object 300 based on the one or more output signals from the reader 104 and the one or more output signals from the impact sensor 600. The processor 108 can determine the frequency of impacts for an operation period of the system 100, for a specified period of time, for an average time span, or the like. In embodiments, the processor 108 can determine the time since a previous impact between the human appendage 114 and the environmental object 300 based on the one or more output signals from the reader 104 and the one or more output signals from the impact sensor 600.

In embodiments, the processor 108 is configured to determine when a distance between the human appendage 114 and the environmental object 300 is less than the threshold distance based on the one or more output signals from the reader 104 and the one or more output signals from the impact sensor 600. The threshold distance can be a predetermined value that corresponds to a safety consideration to prevent or mitigate impact between the human appendage 114 and the environmental object 300. In embodiments, the processor 108 is configured to determine a time corresponding to when the distance between the human appendage 114 and the environmental object 300 became less than the threshold distance based on the one or more output signals from the reader 104 and the one or more output signals from the impact sensor 600. For example, the timing device 400 can be configured to provide a time at which the human appendage 114 and the environmental object 300 came within the threshold distance with respect to each other. In embodiments, the processor 108 is configured to determine a frequency of instances when the distance between the human appendage 114 and the environmental object 300 became less than the threshold distance based on the one or more output signals from the reader 104 and the one or more output signals from the impact sensor 600. The processor 108 can determine the frequency of such instances for an operation period of the system 100, for a specified period of time, for an average time span, or the like. In embodiments, the processor 108 can determine the time since a previous instance of when the human appendage 114 and the environmental object 300 came within the threshold distance with respect to each other based on the one or more output signals from the reader 104 and the one or more output signals from the impact sensor 600.

In embodiments, the memory device 500 can store data associated with an impact or near impact between the human appendage 114 and the environmental object 300, where a determination of the impact is based on the one or more output signals from the reader 104 and the one or more output signals from the impact sensor 600. The data associated with an impact between the human appendage 114 and the environmental object 300 can include, but is not limited to, a time of the impact between the human appendage 114 and the environmental object 300, or a frequency of occurrences of impact between the human appendage 114 and the environmental object 300. In embodiments, the memory device 500 can store data associated with when the distance between the human appendage 114 and the environmental object 300 is less than the threshold distance, where a determination that the distance between the human appendage 114 and the environmental object 300 is less than the threshold distance is based on the one or more output signals from the reader 104 and the one or more output signals from the impact sensor 600. The data associated with when the distance between the human appendage 114 and the environmental object 300 is less than the threshold distance can include, but is not limited to, data associated with when the distance between the human appendage 114 and the environmental object 300 is less than the threshold distance, or a frequency of instances of when the distance between the human appendage 114 and the environmental object 300 is less than the threshold distance.

Figure 7:
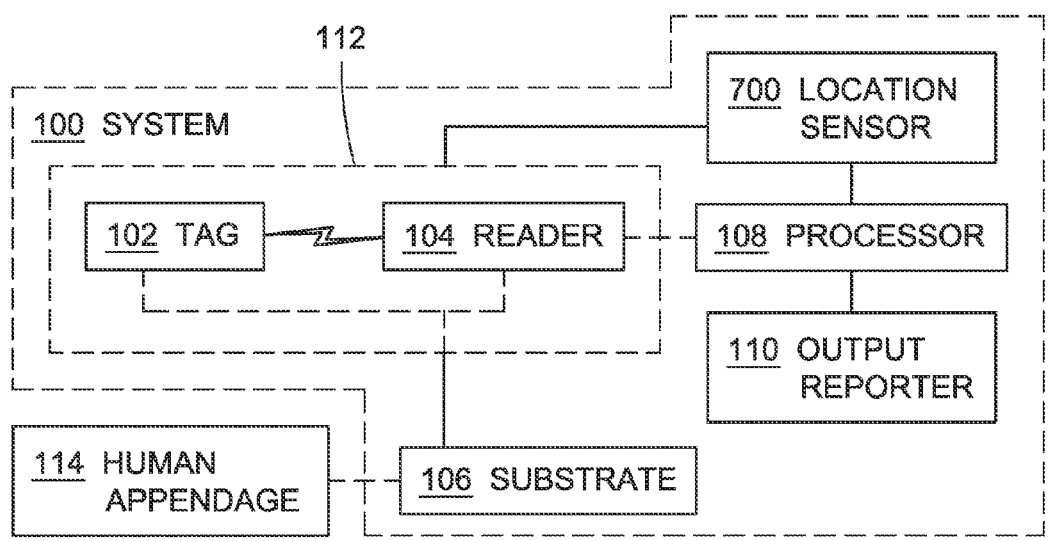
FIG. 7 is a schematic of an embodiment of a system such as shown in FIG. 1.

In embodiments (such as shown in FIG. 7), the system 100 includes a location sensor 700 configured to generate one or more output signals associated with a location (e.g., geographical location, absolute location, relative location, etc.) of at least one of the human appendage 114 or the environmental object 300. In embodiments, the location sensor 700 is configured to determine a location of one or more of the tag 102 or the reader 104, which in embodiments can provide an analog for a location of one or more of the human appendage 114 or the environmental object 300. The location sensor 700 can include, but is not limited to, one or more of a positioning sensor (e.g., a satellite and/or terrestrial-based positioning system, such as a global positioning system, an indoor positional system, a cellular network system, a land mobile radio based system, etc.), an optic sensor (e.g., an imaging device for location recognition), a laser (e.g., laser or laser diode positioning sensors), an acoustic sensor (e.g., acoustic source localization device), or a radar-based sensor (e.g., a frequency modulated continuous wave (FMCW) radar detector/sensor). In embodiments, the location sensor 700 is configured for positioning on the human appendage 114. For example, the location sensor 700 can be coupled to the substrate 106. In embodiments, the location sensor 700 is positioned remote from at least one of the human appendage 114 or the environmental object 300. For example, the location sensor 700 can be configured to remotely determine the location of at least one of the human appendage 114 or the environmental object 300. In embodiments, the location sensor 700 is coupled to the reader 104. For example, the reader 104 can include a location sensor 700 configured to identify a location of the reader 104, which can correspond to a location of one or more of the human appendage 114 or the environmental object 300 depending on where the reader 104 is coupled.

In embodiments, the location sensor 700 includes an accelerometer, which can serve an as initiator for when the location sensor 700 is operable. For example, the location sensor 700 can measure one or more of a distance or a direction from an initiation point based on activation of the accelerometer. Such activation can be due to movement of the human appendage 114 (such as when the reader 104 and location sensor 700 are positioned on the substrate 106 on the human appendage 114), due to impact to the environmental object 300 (such as when the reader 104 and location sensor 700 are positioned on the substrate 106 on either of the human appendage 114 or the environmental object 300), or the like. The initiation point can correspond to one or more of a user reference point (e.g., a position of a user on which the substrate 106 is coupled), an updatable reference point (e.g., a reference point of the environmental object 300), or the like.

In embodiments, the location sensor 700 is configured to interact with a network of location beacons to measure the location of at least one of the reader 104 or the tag 102. For example, the network of location beacons can include, but is not limited to, beacons configured to periodically or continuously transmit data associated with a location of the respective beacon, beacons configured to periodically or continuously transmit data associated with an operation status of the respective beacon, or the like. The beacons can include devices operating under a common communications standard, including but not limited to, Bluetooth communication protocols, RFID communication protocols, or the like.

The processor 108 can be communicatively coupled with the location sensor 700 to receive the one or more output signals from the location sensor 700. In embodiments, the processor 108 is configured to determine that an impact has occurred between the human appendage 114 and the environmental object 300 based at least in part on the one or more output signals from the location sensor 700. For example, the location sensor 700 can track the location of one or more of the human appendage 114 or the environmental object 300, whereby the processor 108 can determine that the location of the human appendage 114 or the environmental object 300 overlaps with or substantially matches a location of the other of the human appendage 114 or the environmental object 300. In embodiments, the memory device 500 stores location information associated with one or more environmental objects 300, where the location sensor 700 tracks the location of the human appendage 114. The processor 108 can compare the tracked location of the human appendage 114 to the stored location information associated with one or more environmental objects 300 to determine whether the human appendage 114 impacted with or more of the environmental objects 300. In embodiments, the processor 108 is configured to determine a time of the impact between the human appendage 114 and the environmental object 300 based on the one or more output signals from the location sensor 700. For example, the timing device 400 (e.g., shown in FIG. 4) can be communicatively coupled with the processor 108, where the processor 108 can access a time from the timing device 400 when the one or more output signals from the location sensor 700 provide an indication that an impact has occurred between the human appendage 114 and the environmental object 300. In embodiments, the processor 108 is configured to determine a frequency of impacts between the human appendage 114 and the environmental object 300 based on the one or more output signals from the location sensor 700. The processor 108 can determine the frequency of impacts for an operation period of the system 100, for a specified period of time, for an average time span, or the like. In embodiments, the processor 108 can determine the time since a previous impact between the human appendage 114 and the environmental object 300 based on the one or more output signals from the location sensor 700.

In embodiments, the processor 108 is configured to determine when a distance between the human appendage 114 and the environmental object 300 is less than the threshold distance based at least in part on the one or more output signals from the location sensor 700. The threshold distance can be a predetermined value that corresponds to a safety consideration to prevent or mitigate impact between the human appendage 114 and the environmental object 300. For example, the location sensor 700 can track the location of one or more of the human appendage 114 or the environmental object 300, whereby the processor 108 can determine a distance between the human appendage 114 and the environmental object 300, in order to determine that the distance is less than a predetermined threshold distance. In embodiments, the processor 108 is configured to determine a time corresponding to when the distance between the human appendage 114 and the environmental object 300 became less than the threshold distance based on the one or more output signals from the location sensor 700. For example, the timing device 400 can be configured to provide a time at which the human appendage 114 and the environmental object 300 came within the threshold distance with respect to each other. In embodiments, the processor 108 is configured to determine a frequency of instances when the distance between the human appendage 114 and the environmental object 300 became less than the threshold distance based on the one or more output signals from the location sensor 700. The processor 108 can determine the frequency of such instances for an operation period of the system 100, for a specified period of time, for an average time span, or the like. In embodiments, the processor 108 can determine the time since a previous instance of when the human appendage 114 and the environmental object 300 came within the threshold distance with respect to each other based on the one or more output signals from the location sensor 700.

In embodiments, the memory device 500 can store data associated with an impact or near impact between the human appendage 114 and the environmental object 300, where a determination of the impact is based at least in part on the one or more output signals from the location sensor 700. The data associated with an impact between the human appendage 114 and the environmental object 300 can include, but is not limited to, a time of the impact between the human appendage 114 and the environmental object 300, or a frequency of occurrences of impact between the human appendage 114 and the environmental object 300. In embodiments, the memory device 500 can store data associated with when the distance between the human appendage 114 and the environmental object 300 is less than the threshold distance, where a determination that the distance between the human appendage 114 and the environmental object 300 is less than the threshold distance is based at least in part on the location sensor 700. The data associated with when the distance between the human appendage 114 and the environmental object 300 is less than the threshold distance can include, but is not limited to, data associated with when the distance between the human appendage 114 and the environmental object 300 is less than the threshold distance, or a frequency of instances of when the distance between the human appendage 114 and the environmental object 300 is less than the threshold distance.

Figure 8:
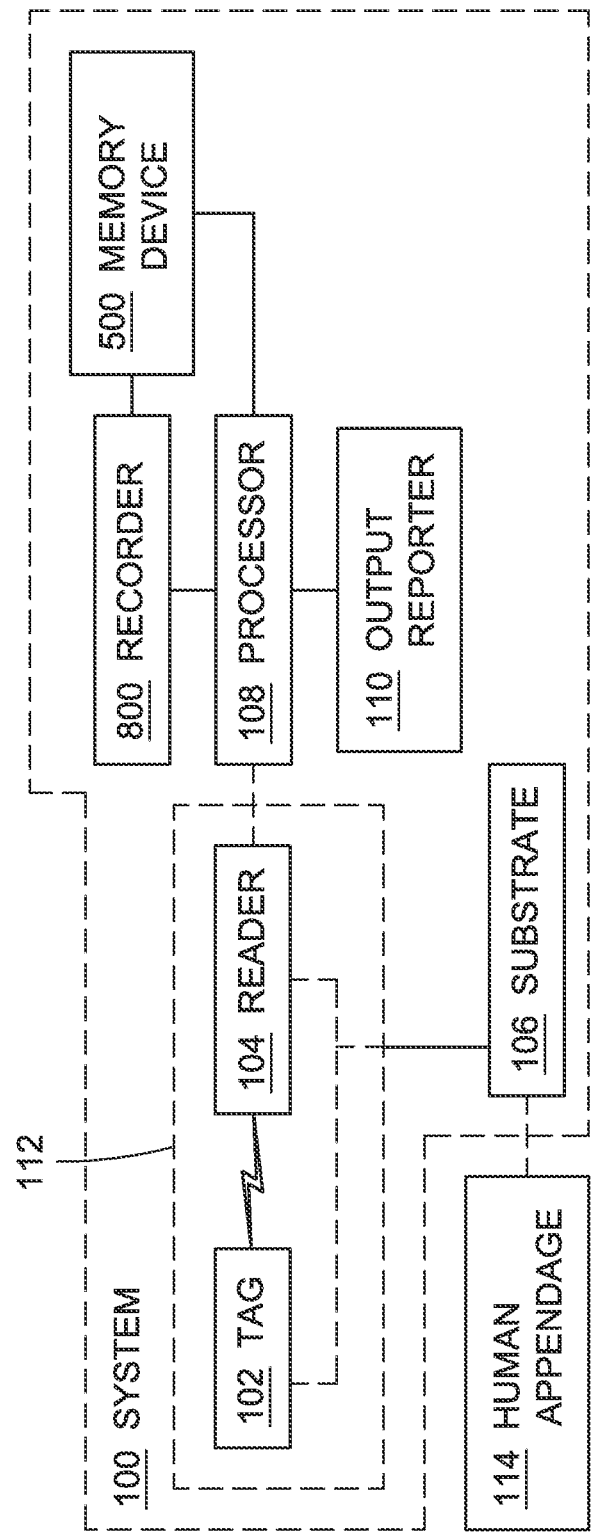
FIG. 8 is a schematic of an embodiment of a system such as shown in FIG. 1.

In embodiments (such as shown in FIG. 8), the system 100 can include a recorder 800 operably coupled to the processor 108. In general, the recorder 800 is configured to record, store, or the like, data, output signals, and communication signals generated by one or more components of the system 100. For example, the recorder 800 can be configured to record the one or more output signals from the reader 104 in a memory device, such as the memory device 500. In embodiments, the recorder 800 is configured to store in the memory device 500 data associated with an impact between the human appendage 114 and the environmental object 300. Such data can include, but is not limited to, a time of impact, a location of impact, or a frequency of impact. In embodiments, the recorder 800 is configured to store in the memory device 500 data associated with when the distance between the human appendage 114 and the environmental object 300 is less than the threshold distance. Such data can include, but is not limited to, a time corresponding to when the distance between the human appendage 114 and the environmental object 300 is less than the threshold distance, a location corresponding to when the distance between the human appendage 114 and the environmental object 300 is less than the threshold distance, or a frequency of instances of when the distance between the human appendage 114 and the environmental object 300 is less than the threshold distance.

In embodiments, the processor 108 can be configured to make determinations regarding one or more physical aspects associated with at least one of the human appendage 114 and the environmental object 300. For example, the processor 108 can be configured to determine a force of an impact between the human appendage 114 and the environmental object 300. The processor 108 can access data from one or more sensors of the system 100 to make such determinations. For example, the processor 108 can access data from a force sensor, from a pressure sensor, from an accelerometer, or the like. In embodiments, the processor 108 is configured to determine what a force of a potential impact would be, should such potential impact actually occur. For example, the processor 108 can determine, based on at least a current or previous velocity, speed, or the like of the human appendage 114, what force the human appendage 114 would impact the environmental object 300 should the human appendage 114 and the environmental object 300 actually collide. In embodiments, the processor 108 can extrapolate and/or interpolate one or more of positional data, speed data, velocity data, or acceleration data to estimate or predict the force at which the human appendage 114 and the environmental object 300 would collide.

Figure 9:
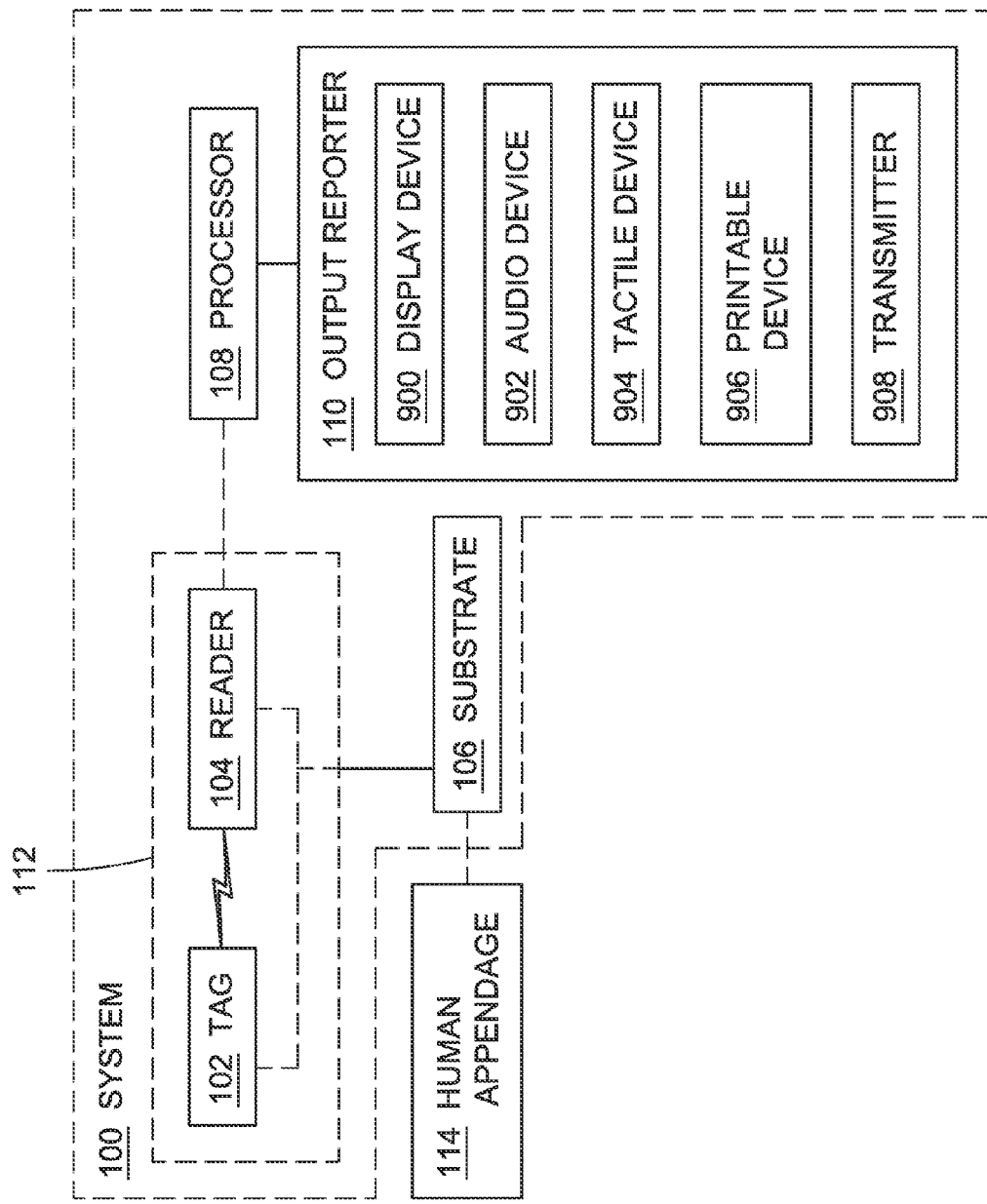
FIG. 9 is a schematic of an embodiment of a system such as shown in FIG. 1.

The output reporter 110 is configured to generate one or more communication signals to report information associated with operation of the system 100. In embodiments, the output reporter 110 is configured to generate one or more communication signals responsive to instruction by the processor 108. The information from the output reporter 110 may be provided one or more of visually (e.g., via transmission, printing information, or display of visual information), audibly (e.g., via transmission or display of auditory information), tactually (e.g., via presentation of tactile information), or as data (e.g., via transmission or display of one or more data signals associated with the information to convey). The output reporter 110 may function in combination with the processor 108 to provide visual, auditory, or tactile information associated with the human appendage 114 and/or the environmental object 300, such as the proximity of the human appendage 114 with respect to the environmental object 300, impact information, threshold information, recommendations for action with respect to the environmental object 300, or the like. In embodiments, such as shown in FIG. 9, the output reporter 110 includes a display device 900 configured to report, communicate, or otherwise provide information to a user of the system 100, such as to provide visual (e.g., graphical, textual, etc.) indications of the information associated with operation of the system 100. The display device 900 can include, but is not limited to, one or more of a graphical user interface (GUI), a touchscreen assembly (e.g., a capacitive touch screen), a liquid crystal display (LCD), a light-emitting diode (LED) display, or a projection-based display. As shown in FIG. 9, the output reporter 110 can include one or more of an audio device 902, configured to provide auditory indications of the information associated with operation of the system 100, a tactile device (e.g., a vibration device), configured to provide tactile indications of the information associated with operation of the system 100, a printing device 906, configured to print a tangible/physical indication of the information associated with operation of the system 100, or a transmitter 908, configured to transmit information from the system 100 to an external device or location (e.g., a remote entity, a remote device (e.g., an alarm positioned in the subject's room, a healthcare provider's room, a third party computing device, or so forth), a remote server, a remote network (e.g., a LAN (local area network), a BAN (body area network), a smart house, or so forth), an external device associated with an external network that includes one or more of a health provider network, an insurance network, a personal health record, or a personal health database, or so forth). In embodiments, the external device includes a communication device, such as one or more of a mobile communication device or a computer system including, but not limited to, mobile computing devices (e.g., hand-held portable computers, Personal Digital Assistants (PDAs), laptop computers, netbook computers, tablet computers, or so forth), mobile telephone devices (e.g., cellular telephones and smartphones), devices that include functionalities associated with smartphones and tablet computers (e.g., phablets), portable game devices, portable media players, multimedia devices, satellite navigation devices (e.g., Global Positioning System (GPS) navigation devices), e-book reader devices (eReaders), Smart Television (TV) devices, surface computing devices (e.g., table top computers), Personal Computer (PC) devices, and other devices that employ touch-based human interfaces. The output reporter 110 can communicate (e.g., send and receive communication signals) with the external device via one or more connected and wireless communication mechanisms including, but not limited to acoustic communication signals, optical communication signals, radio communication signals, infrared communication signals, ultrasonic communication signals, and the like.

In embodiments, the output reporter 110 generates (e.g., via the display device 900) a graphical representation of data associated with operation of the system 100. The graphical representation can include a map-based display of the information, which can provide the data with respect to absolute or relative locations. The map can correspond to a region proximate one or more environmental objects 300 and can display information associated with interaction between the human appendage 114 and the one or more environmental objects. For example, the map can indicate frequency of impact (or near impact) between the human appendage 114 and various environmental objects 300 where the data is color-coded to differentiate between differing frequencies. Other presentations of data are possible, including but not limited to, topographical plots, bar plots, pie plots, or the like. As another example, the map can indicate time of impact (or near impact) between the human appendage 114 and various environmental objects 300 where the data is coded to differentiate between differing times of impact (or near impact).

In embodiments, the processor 108 is configured to generate a recommendation based on one or more output signals from one or more of the reader 104, the impact sensor 600, or the location sensor 700. The recommendation can include, but is not limited to, a recommendation pertaining to the environmental object 300, where such recommendation can reduce at least one of a likelihood of impact with the environmental object 300 or a degree of severity of impact with the environmental object 300. For example, in embodiments, the recommendation includes a recommendation to reposition the environmental object 300 to a new location within the environment. The new location within the environment can be a location that an individual is less likely to impact with the environmental object 300 as compared to the previous location (i.e., the location prior to the recommendation to reposition the environmental object 300). For example, the processor 108 can access (e.g., from the memory device 500) one or more modules configured to analyze the positioning of the environmental object 300 based on one or more output signals from one or more of the reader 104, the impact sensor 600, or the location sensor 700. Where the processor 108 determines that the current position of the environmental object 300 results in too many impacts (e.g., the number of impacts between the human appendage 114 and the environmental object 300 exceeds a threshold impact value), the processor 108 can generate the recommendation to reposition the environmental object 300 to a new location within the environment. The new location within the environment can include one or more of a different location within the environment than the previous position prior to the recommendation to reposition the environmental object 300, a location within a threshold distance from the previous position, a location outside of a threshold distance from the previous position, a location determined to have a probability of fewer impacts between the human appendage 114 and the environmental object 300, or so forth. In embodiments, the processor 108 conveys the recommendation to reposition the environmental object 300 via the output reporter 110. For example, the output reporter 110 can generate one or more of a visual indication of the recommendation (e.g., via the display device 900), an audible indication of the recommendation (e.g., via the audio device 902), a tactile indication of the recommendation (e.g., via the tactile device 904), a physical indication of the recommendation (e.g., via the printing device 906), or a transmitted indication via one or more data signals (e.g., via the transmitter 908).

In embodiments, the processor 108 is configured to generate a visible recommendation associated with a map corresponding to a region proximate the environmental object 300. The processor 108 can generate the map via the output reporter 110 to provide the visible recommendation. The map can include information including but not limited to, a recommended location to reposition the environmental object 300, a listing of areas proximate the environmental object 300 within the environment to which the environmental object 300 can be repositioned, a region proximate the environmental object 300 within a threshold distance, a region corresponding to locations outside of a threshold distance from the environmental object 300, data associated with impact frequency associated with one or more environmental objects, or so forth. For example, in embodiments, the processor 108 generates the map via the output reporter 110, wherein the map provides a visual distinction between varying intensities of impact between respective environmental objects (e.g., lower wavelength colors for areas corresponding to more impacts, higher wavelength colors for areas corresponding to fewer impacts, etc.).

In embodiments, the recommendation generated by the processor 108 includes a recommendation to provide the environmental object 300 with a cushioning material. The cushioning material can reduce a degree of severity of impact with the environmental object 300 by absorbing or mitigating at least a portion of the force of impact between the human appendage 114 and the environmental object 300. For example, cushioning material can include, but is not limited to, fibrous materials (e.g., synthetic fibers, fabric, felt, paper, cardboard, feather, etc.), polymeric materials (e.g., foam, memory foam, rubber, polystyrene, polypropylene, polyethylene, polyurethane, etc.), entrapped gas material (e.g., air cushions, gas enclosed within plastic film, etc.), mechanical devices (e.g., shock absorber, spring-based device, pneumatic device, etc.), or the like. The processor 108 can access (e.g., from the memory device 500) one or more modules configured to analyze force of impacts between the environmental object 300 and another object (e.g., the human appendage 114) based on one or more output signals from one or more of the reader 104, the impact sensor 600, or the location sensor 700. In embodiments, when the processor 108 determines that one or more impacts with the environmental object 300 results in a force of impact that exceeds a threshold force of impact value, the processor 108 can generate the recommendation to provide the environmental object 300 with a cushioning material to reduce or mitigate the force of subsequent impacts with the environmental object 300. In embodiments, the processor 108 conveys the recommendation to provide the cushioning material to the environmental object 300 via the output reporter 110. For example, the output reporter 110 can generate one or more of a visual indication of the recommendation (e.g., via the display device 900), an audible indication of the recommendation (e.g., via the audio device 902), a tactile indication of the recommendation (e.g., via the tactile device 904), a physical indication of the recommendation (e.g., via the printing device 906), or a transmitted indication via one or more data signals (e.g., via the transmitter 908).

In embodiments, the recommendation generated by the processor 108 includes a recommendation to provide the environmental object 300 with a visible indicator. The visible indicator can reduce the likelihood of impact between the human appendage 114 and the environmental object 300 by providing a visual indication associated with the position of the environmental object 300 within the environment. For example, the visual indicator can include a visible light source that can be placed on/near the environmental object 300 to provide an individual with a visual indication associated with the position of the environmental object 300 within the environment. The visible light source can illuminate at least a portion of the environmental object 300, which can assist an individual in viewing the environmental object 300, such as during periods of darkness within the environment (e.g., nighttime, power failure, etc.). In embodiments, the processor 108 is configured to activate the visual indicator based upon one or more output signals from one or more of the reader 104, the impact sensor 600, or the location sensor 700. For example, the output signals from one or more of the reader 104, the impact sensor 600, or the location sensor 700 can provide an indication that the human appendage 114 is within a threshold distance from the environmental object 300, whereby the processor 108 activates the visual indicator to provide a warning to the individual regarding a potential impact with the environmental object 300.

In embodiments, the recommendation generated by the processor 108 includes a recommendation to provide the environmental object 300 with an audible indicator. The audible indicator can reduce the likelihood of impact between the human appendage 114 and the environmental object 300 by providing an auditory indication associated with the position of the environmental object 300 within the environment. For example, the audible indicator can include an alarm device or speaker device that can be placed on/near the environmental object 300 to provide an individual with an auditory indication associated with the position of the environmental object 300 within the environment. The audible indicator can alert an individual to the presence of the environmental object 300, which can assist an individual in avoiding contact or impact with the environmental object 300, such as during periods of darkness within the environment (e.g., nighttime, power failure, etc.), for individuals with visual impairments, or the like. In embodiments, the processor 108 is configured to activate the audible indicator based upon one or more output signals from one or more of the reader 104, the impact sensor 600, or the location sensor 700. For example, the output signals from one or more of the reader 104, the impact sensor 600, or the location sensor 700 can provide an indication that the human appendage 114 is within a threshold distance from the environmental object 300, whereby the processor 108 activates the audible indicator to provide a warning to the individual regarding a potential impact with the environmental object 300.

In embodiments, the output reporter 110 is configured to generate an alert responsive to instruction by the processor 108 when a distance between the human appendage 114 and the environmental object 300 is less than a threshold distance. The environmental object 300 can be identified by the system 100 as at least one of a risk for impact with the human appendage 114 or a previously impacted object (e.g., previously impact by the human appendage 114, another environmental object, etc.). For example, the processor 108 can access (e.g., from the memory device 500) one or more modules configured to analyze a position of a particular environmental object 300 (or an analog for the environmental object, such as the tag 102, the reader 104, etc.) relative to the human appendage 114 (or an analog for the human appendage 114, such as the tag 102, the reader 104, etc.) based at least in part on one or more output signals from one or more of the reader 104, the impact sensor 600, or the location sensor 700 to determine a distance between the human appendage 114 and the environmental object 300. The processor 108 can then compare the determined distance between the human appendage 114 and the environmental object 300 to a threshold distance to determine whether the determined distance is less than the threshold distance. The threshold distance can be a stored value that can depend on spacing considerations (e.g., constraints of the size of the environment), can depend on particular environmental objects (e.g., more dangerous environmental objects can have a larger attributed threshold distance), or the like. Such comparison can occur on a periodic basis, a continuous basis, or the like. Where the processor 108 determines that the distance between the environmental object 300 and the human appendage 114 is less than the threshold distance, the processor 108 can instruct the output reporter 110 to generate an alert. In embodiments, the alert can be one or more of an audible alert, a visual alert, or a tactile alert.

In embodiments, the alert is associated with the human appendage 114. An alert associated with the human appendage 114 can include, but is not limited to, one or more of an alert displayed on the human appendage 114, an alert projected to the human appendage 114 (e.g., from a location remote from the human appendage 114), an alert indicating the human appendage 114, or the like. For example, the alert can include, but is not limited to, an alert originating from a device on the human appendage 114, an alert indicating or identifying the human appendage 114 (e.g., displaying the alert on a screen that provides at least an indication of the human appendage 114, such as by accentuating an area, region, object, etc. on a map), a visual or audible alert projected from a device onto the human appendage 114 (e.g., directing light or sound at the human appendage 114), or the like. In embodiments, the alert is associated with the environmental object 300. An alert associated with the environmental object 300 can include, but is not limited to, one or more of an alert displayed on the environmental object 300, an alert projected to the environmental object 300 (e.g., from a location remote from the environmental object 300), an alert indicating the environmental object 300, or the like. For example, the alert can include, but is not limited to, an alert originating from a device on the environmental object 300, an alert indicating or identifying the environmental object 300 (e.g., displaying the alert on a screen that provides at least an indication of the environmental object 300, such as by accentuating an area, region, object, etc. on a map), a visual or audible alert projected from a device onto environmental object 300 (e.g., directing light or sound at the environmental object 300), or the like.

Figure 10:
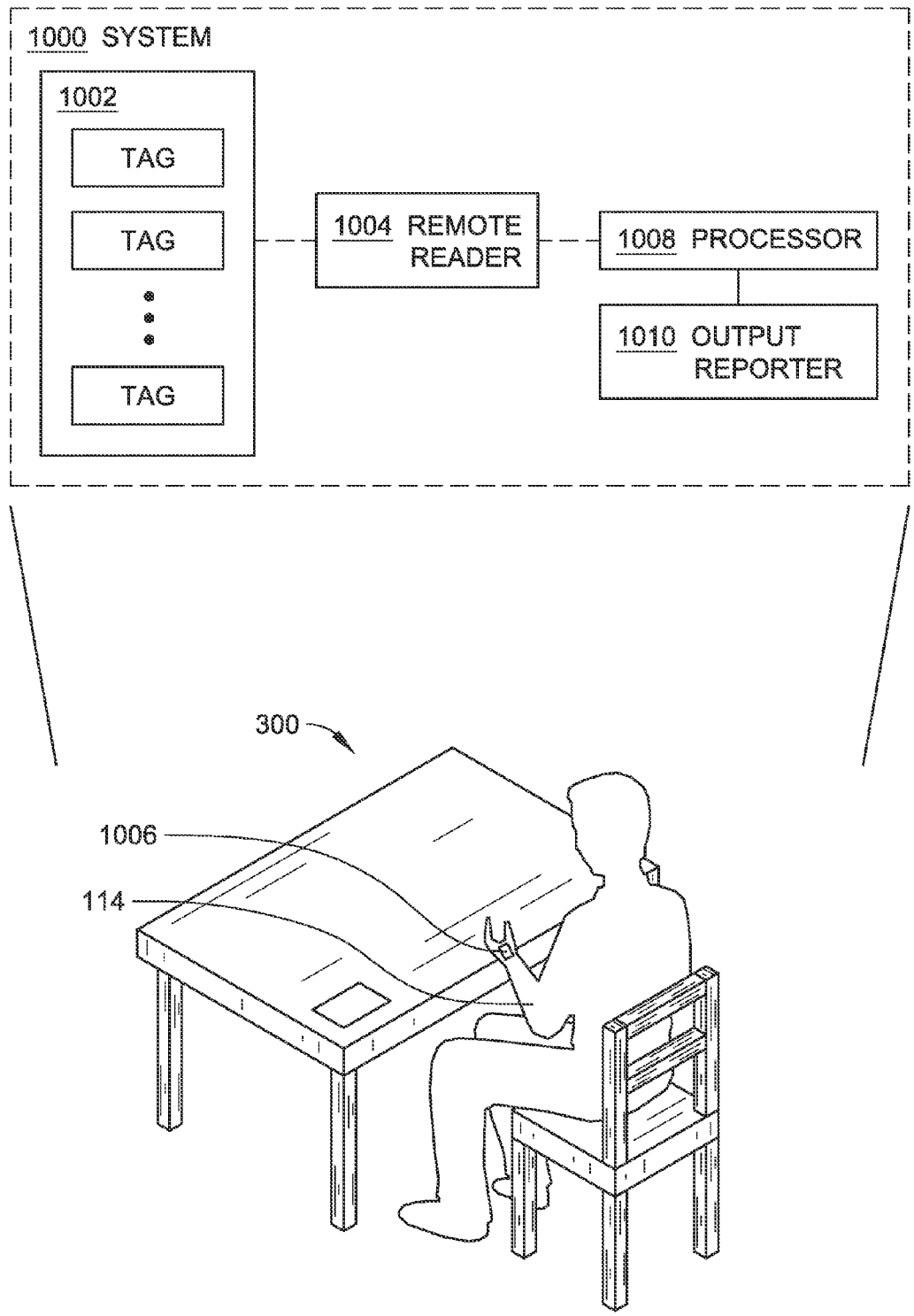
FIG. 10 is a schematic of a system with interactive management of environmental objects relative to human appendages.
Figure 11:
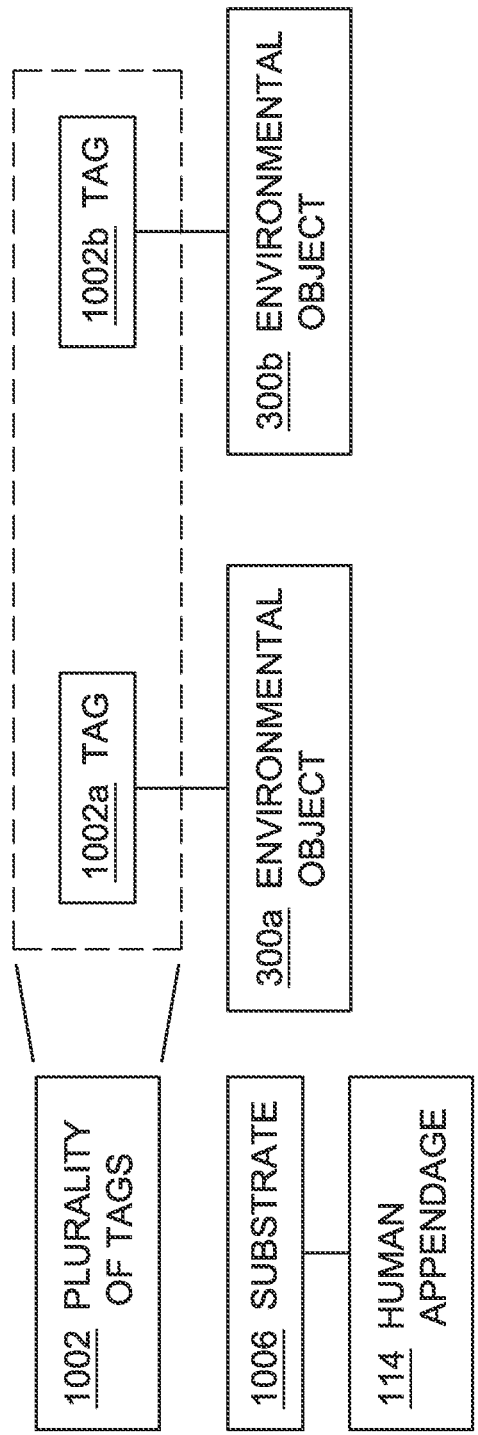
FIG. 11 is a schematic of an embodiment of a system such as shown in FIG. 10.

In embodiments, as shown in FIG. 10, a system 1000 is configured to monitor an environment through which an individual can move, where the system can identify environmental objects in proximity to an appendage of the individual to aid in preventing damage to the individual and/or the environmental object associated with physical impact between the environmental object and the appendage. The system 1000 includes a plurality of tags 1002, a remote reader 1004, a processor 1008, and an output reporter 1010. As shown in FIG. 11, the plurality of tags 1002 includes at least one tag 1002 that is configured to be coupled to a substrate 1006, where the substrate 1006 is conformable to the human appendage 114. The plurality of tags 1002 also includes at least one other tag 1002 configured to be coupled to an environmental object 300. For example, as shown in FIG. 11, the plurality of tags 1002 can include a first tag 1002a configured to be coupled to a first environmental object 300a and a second tag 1002b configured to be coupled to a second environmental object 300b. While two tags 1002 and two environmental objects 300 are shown, the system 1000 is not limited to two tags 1002 and two environmental objects 300, and can, for example, include three or more tags 1002 and three or more environmental objects 300. In embodiments, the tags of the plurality of tags 1002 can correspond to the tags 102 described herein, including but not limited to the structural and functional characteristics thereof. In embodiments, the remote reader 1004 can correspond to the reader 104 described herein, including but not limited to the structural and functional characteristics thereof. For example, the tags of the plurality of tags 1002 can include, but are not limited to a radio frequency identification (RFID) tag, where the remote reader 1004 can include, but is not limited to an RFID reader. The tags of the plurality of tags 1002 can also include, but are not limited to a magnetic material (e.g., a diamagnetic material, a paramagnetic material, a ferromagnetic material, etc.), where the remote reader 1004 can include, but is not limited to a magnetic detector (e.g., a magnetic field detector, a magnetometer, etc.). The tags of the plurality of tags 1002 can also include, but are not limited to a metallic material, where the remote reader 1004 can include, but is not limited to a magnetic material configured to at least one of identify or detect the metallic material. The tags of the plurality of tags 1002 can also include, but are not limited to an optical label (e.g., a bar code, a matrix barcode (e.g. QR code), etc.), where the remote reader 1004 can include, but is not limited to an optical reader (e.g., a camera, an imaging device, etc.).

In embodiments, the remote reader 1004 is configured to distinctly identify each tag of the plurality of tags 1002. For example, the remote reader 1004 can distinctly identify the tag 1002 coupled to the substrate 1006, can distinctly identify the tag 1002*a* coupled to the environmental object 300*a*, can distinctly identify the tag 1002*b* coupled to the environmental object 300*b*, or so forth. The distinct identification of the tags 1002 by the remote reader 1004 can depend on one or more of the structural composition of the tags 1002, a location of the tags 1002, a unique identifier associated with each tag of the plurality of tags 1002, or so forth. For example, the structural composition of each tag of the plurality of tags 1002 can differ from other tags of the plurality of tags 1002 such that the remote reader 1004 can differentiate each tag from the other tags. In embodiments, the remote reader 1004 is configured to sense respective tags of the plurality of tags 1002. The sensing can include, but is not limited to, recognizing the presence of the respective tags of the plurality of tags 1002. For example, the sensing of respective tags can include, but is not limited to sensing the tag 1002 coupled to the substrate 1006, sensing the tag 1002*a* coupled to the environmental object 300*a*, sensing the tag 1002*b* coupled to the environmental object 300*b*, or so forth.

The processor 1008 is operably coupled to the remote reader 1004 and is configured to receive one or more output signals from the remote reader 1004. The processor 1008 and the remote reader 1004 can communicate via wired or wireless communication protocols such that the processor 1008 receives the one or more output signals from the remote reader 1004. For example, the processor 1008 can be positioned remotely from the remote reader 1004, positioned adjacent to the remote reader 1004, coupled to the remote reader 1004 and the substrate 1006, or the like. In general, the one or more output signals from the remote reader 1004 correspond to information associated with one or more of the plurality of tags 1002, including but not limited to the association of one or more of the plurality of tags 1002 relative to another tag of the plurality of tags 1002. For example, the one or more output signals from the remote reader 1004 can correspond to a threshold associated with the at least one tag 1002 coupled to the substrate 1006 and at least one other tag 1002 coupled to an environmental object 300. In embodiments, the threshold associated with the at least one tag 1002 coupled to the substrate 1006 and at least one other tag 1002 coupled to an environmental object 300 is a distance threshold between the at least one tag 1002 coupled to the substrate 1006 and at least one other tag 1002 coupled to the environmental object 300, where the processor 1008 can process the one or more output signals to make a determination regarding when the respective tags 1002 are at a distance that is less than the distance threshold. The distance threshold can correspond to a value indicative of an impending impact, or a near miss, such that when a distance between the respective tags 1002 is less than the threshold distance, the respective tags 1002 can be at risk for impact with each other. For example, in embodiments, the distance threshold is between about one-eighth inch and about ten feet, although other distance thresholds can be utilized which can depend on the configuration of the environment and the environmental object(s) 300. In embodiments, the threshold associated with the at least one tag 1002 coupled to the substrate 1006 and at least one other tag 1002 coupled to an environmental object 300 is a frequency threshold between the respective tags 1002. The frequency threshold can correspond to a frequency of occurrences associated with the respective tags 1002, such as a frequency of occurrence of impact between the respective tags 1002, a frequency of occurrence of near impact (e.g., a distance less than the threshold distance) between the respective tags 1002, a frequency of occurrence of interaction between the respective tags 1002, a frequency of occurrence of identification by the remote reader 1004 of one or more of the plurality of tags 1002, a frequency of occurrence of detection by the remote reader 1004 of one or more of the plurality of tags 1002, or the like. The processor 1008 can process the one or more output signals associated with the frequency threshold to make a determination pertaining to a frequency of occurrences between the at least one tag 1002 coupled to the substrate 1006 and at least one other tag 1002 coupled to an environmental object 300.

In embodiments, the processor 1008 can correspond to the processor 108 described herein, including but not limited to the structural and functional characteristics thereof. The processor 1008 includes components to process the one or more output signals from the remote reader 1004 and to provide instruction to the output reporter 1010 to generate one or more communication signals associated with one or more of data associated with the one or more output signals or determinations made by the processor 1008. For example, the processor 1008 can include a microprocessor, a central processing unit (CPU), a digital signal processor (DSP), an application-specific integrated circuit (ASIC), a field programmable gate entry (FPGA), or the like, or any combinations thereof, and can include discrete digital or analog circuit elements or electronics, or combinations thereof. In one embodiment, the computing device includes one or more ASICs having a plurality of predefined logic components. In one embodiment, the computing device includes one or more FPGAs having a plurality of programmable logic commands.

In embodiments, the processor 1008 is configured to determine that an impact has occurred between the human appendage 114 and the environmental object 300 based on the one or more output signals from the remote reader 1004. For example, an interaction or impact between at least one tag 1002 coupled to the substrate 1006 and at least one other tag 1002 coupled to the environmental object 300 can be used as a proxy for determining an impact has occurred between the human appendage 114 and the environmental object 300. In embodiments, the processor 1008 is configured to determine a location of impact between the human appendage 114 and the environmental object 300. For example, the distinct identity of a tag of the plurality of tags 1002 can be associated with a location of the tag 1002 in the environment. In embodiments, the characteristics of the tags of the plurality of tags 1002 are stored in a memory device (e.g., memory device 1300). By identifying which tag of the plurality of tags 1002 has been impacted, the processor 1008 can determine the location of the impact based on the correlation between the distinct identity and the location of the tags 1002. In embodiments, the distinct identity of the tags of the plurality of tags 1002 is associated with a unique identifier that is independent of a location of the respective tags. For example, the unique identifier can include information associated with, but not limited to, a previously impacted tag/object, a particular human appendage (e.g., differentiating between body portions, such as left foot from right foot, etc.), a particular individual (e.g., differentiating between different persons or users), a particular feature or characteristic(s) of an environmental object (e.g., a characterization of a soft environmental object differentiated from a characterization of a hard environmental object, etc.), a prioritization of environmental objects 300 (e.g., disregarding output signals associated with impact or near impact with one environmental object, while prioritizing output signals associated with impact or near impact with a prioritized environmental object), or so forth.

Figure 12:
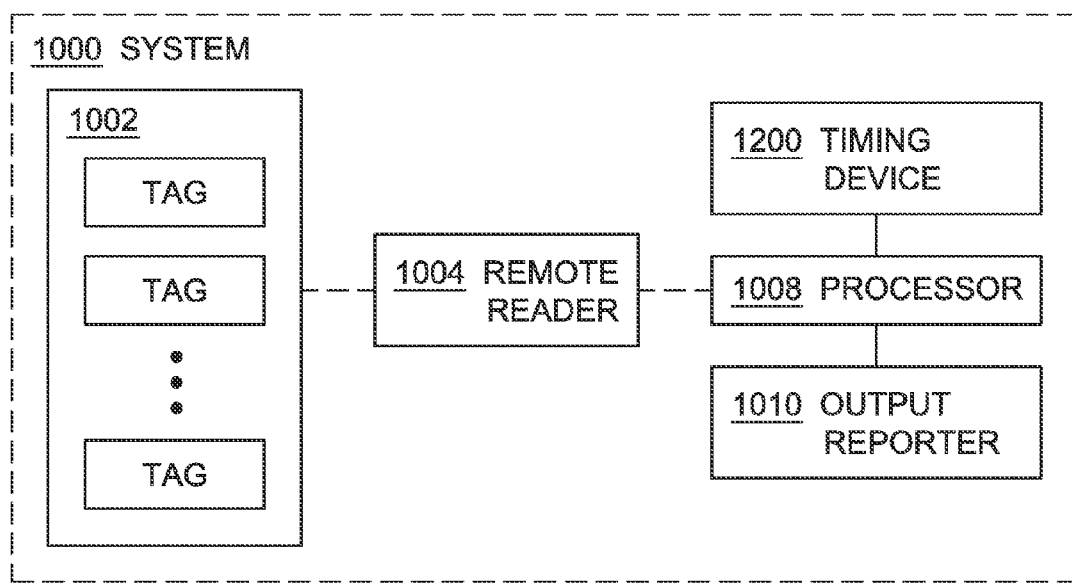
FIG. 12 is a schematic of an embodiment of a system such as shown in FIG. 10.

In embodiments, the processor 1008 is configured to determine a time of the impact between the human appendage 114 and the environmental object 300 based on the one or more output signals from the remote reader 1004. For example, as provided in FIG. 12, the system 1000 can include a timing device 1200 communicatively coupled with the processor 1008 and configured to provide a time at which the human appendage 114 and the environmental object 300 impact each other. In embodiments, the timing device 1200 can correspond to the timing device 400 described herein, including but not limited to the structural and functional characteristics thereof. The timing device 1200 can include, but is not limited to a mechanical timing device, an electromechanical timing device, an electrical timing device, a programmable logic controller, a hardware timing device, or the like. In embodiments, the processor 1008 is configured to determine a frequency of impacts between the human appendage 114 and the environmental object 300 based on the one or more output signals from the remote reader 1004. The processor 1008 can determine the frequency of impacts for an operation period of the system 1000, for a specified period of time, for an average time span, or the like. In embodiments, the processor 1008 can determine the time since a previous impact between the human appendage 114 and the environmental object 300 based on the one or more output signals from the remote reader 1004.

In embodiments, the processor 1008 is configured to determine when a distance between the human appendage 114 and the environmental object 300 is less than the threshold distance based on the one or more output signals from the remote reader 1004. Such determination can provide an indication that the human appendage 114 and the environmental object 300 are within sufficient proximity to pose a threat for impact with one another, or missed impacting each other by a margin that is less than the threshold distance (e.g., a near impact). For example, an impact between at least one tag 1002 coupled to the substrate 1006 and at least one other tag 1002 coupled to the environmental object 300 (e.g., as sensed by the remote reader 1004) can be used as a proxy for determining that the human appendage 114 and the environmental object 300 are at a distance from each other that is less than the threshold distance. The threshold distance can be a predetermined value that corresponds to a safety consideration to prevent or mitigate impact between the human appendage 114 and the environmental object 300. In embodiments, the processor 1008 is configured to determine a time corresponding to when the distance between the human appendage 114 and the environmental object 300 became less than the threshold distance based on the one or more output signals from the remote reader 1004. The timing device 1200 can be configured to provide a time at which the human appendage 114 and the environmental object 300 came within the threshold distance with respect to each other. For example, when the processor 1008 determines that the human appendage 114 and the environmental object 300 are within the threshold distance with respect to each other, the processor 1008 can refer to the timing device 1200 to receive the current time from the timing device 1200. In embodiments, the processor 1008 is configured to determine a frequency of instances when the distance between the human appendage 114 and the environmental object 300 became less than the threshold distance based on the one or more output signals from the remote reader 1004. The processor 1008 can determine the frequency of such instances for an operation period of the system 1000, for a specified period of time, for an average time span, or the like. In embodiments, the processor 1008 can determine the time since a previous instance of when the human appendage 114 and the environmental object 300 came within the threshold distance with respect to each other based on the one or more output signals from the remote reader 1004.

Figure 13:
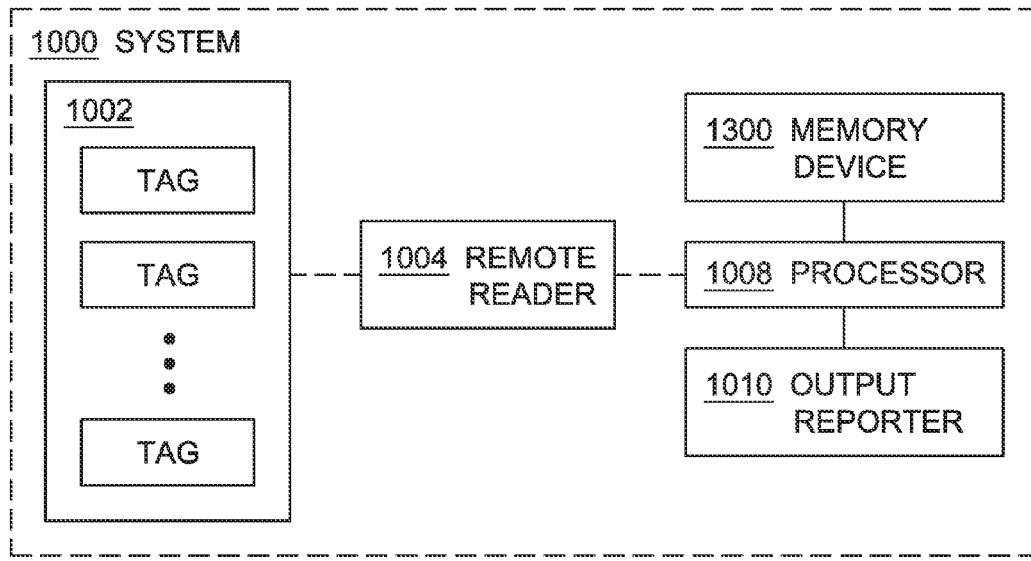
FIG. 13 is a schematic of an embodiment of a system such as shown in FIG. 10.

In embodiments (such as shown in FIG. 13), the system 1000 includes a memory device 1300 configured to store data associated with operation of the system 1000, such as data associated with at least one tag 1002 coupled to the substrate 1006 and at least one other tag 1002 coupled to the environmental object 300. In embodiments, the memory device 1200 can correspond to the memory device 500 described herein, including but not limited to the structural and functional characteristics thereof. The memory device 1300 can include, but is not limited to, a computer memory device, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other medium which can be used to store the desired information maintained by the system 1000 and which can be accessed by the processor 1008, the output reporter 1010, or other associated accessing device. In embodiments, the memory device 1300 can store data associated with an impact or near impact between the human appendage 114 and the environmental object 300. The data associated with an impact between the human appendage 114 and the environmental object 300 can include, but is not limited to, a time of the impact between the human appendage 114 and the environmental object 300, or a frequency of occurrences of impact between the human appendage 114 and the environmental object 300. In embodiments, the memory device 1300 can store data associated with when the distance between the human appendage 114 and the environmental object 300 is less than the threshold distance. The data associated with when the distance between the human appendage 114 and the environmental object 300 is less than the threshold distance can include, but is not limited to, data associated with when the distance between the human appendage 114 and the environmental object 300 is less than the threshold distance, or a frequency of instances of when the distance between the human appendage 114 and the environmental object 300 is less than the threshold distance.

Figure 14:
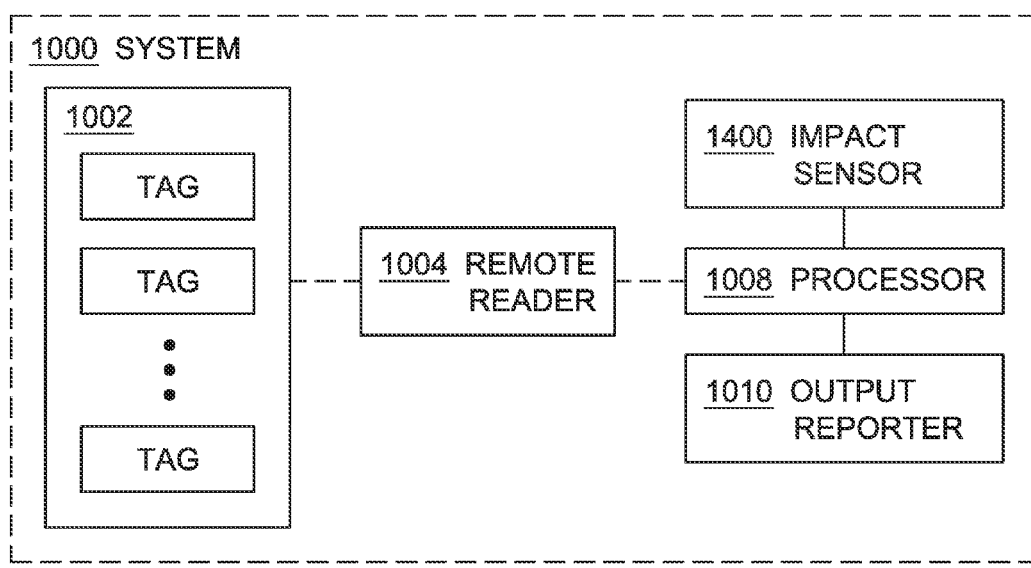
FIG. 14 is a schematic of an embodiment of a system such as shown in FIG. 10.

In embodiments (such as shown in FIG. 14), the system 1000 includes an impact sensor 1400 configured to provide one or more output signals corresponding to a detected impact or near impact associated with at least one tag 1002 coupled to the substrate 1006 and at least one other tag 1002 coupled to the environmental object 300. The impact sensor 1400 can include, but is not limited to, one or more of a proximity sensor, a pressure sensor, or an accelerometer. For example, the impact sensor 600 can include multiple (i.e., more than one) sensors of the proximity sensor, the pressure sensor, and the accelerometer, such as both of a proximity sensor and a pressure sensor, each of a proximity sensor, a pressure sensor, and an accelerometer, or so forth. The proximity sensor can include one or more of an optical proximity sensor, an acoustic proximity sensor, or an electromagnetic proximity sensor. The optical proximity sensor, the acoustic proximity sensor, and the electromagnetic proximity sensor can be configured to emit signals and detect reflected signals in accordance with their specific detection protocols. An optical proximity sensor can detect one or more optical signals (e.g., one or more optical electromagnetic signals) and generate one or more sense signals in response thereto. For example, an optical proximity sensor of the impact sensor 1700 can be configured to detect and/or identify an environmental object 300 and/or a human appendage 114, and their proximity relative to components of the system 1000 based on detected optical signals. The optical sensor can include, but is not limited to, a photodetector (e.g., to detect one or more electromagnetic signals reflected from a surface of an object), an imaging device (e.g., a camera to generate a visual image of one or more objects in proximity to components of the system 1000), or the like. For example, an optical proximity sensor of the impact sensor 1400 can be configured to emit a light signal and detect a reflected light signal, for example a reflected light signal that is reflected by an environmental object 300 and/or a human appendage 114. The acoustic proximity sensor can detect and/or identify objects and their proximity relative to components of the system 1000 based on detected acoustic signals. For example, an acoustic proximity sensor of the impact sensor 1700 can be configured to detect and/or identify an environmental object 300 and/or a human appendage 114, and their proximity relative to components of the system 1000 based on detected acoustic signals. For example, an acoustic proximity sensor of the impact sensor 1400 can be configured to emit an acoustic signal and detect a reflected signal, for example a reflected acoustic signal that is reflected by an environmental object 300 and/or a human appendage 114. The acoustic proximity sensor can include, but is not limited to, sensors configured to detect ultrasonic signals, radio-frequency signals, or the like. An electromagnetic proximity sensor can detect and/or identify objects and their proximity relative to components of the system 1000 based on detected electromagnetic signals. For example, an electromagnetic proximity sensor of the impact sensor 1700 can be configured to detect and/or identify an environmental object 300 and/or a human appendage 114, and their proximity relative to components of the system 1000 based on detected electromagnetic signals. For example, an electromagnetic proximity sensor of the impact sensor 1400 can be configured to emit an electromagnetic signal and detect a reflected electromagnetic signal, for example a reflected electromagnetic signal that is reflected by an environmental object 300 and/or a human appendage 114. The electromagnetic proximity sensor can include, for example, a bolometer or a thermal imaging device (e.g., to measure incident electromagnetic radiation of objects in proximity to components of the system 1000). In embodiments, the impact sensor 1400 includes a pressure sensor configured to sense a direct impact, such as an impact between the environmental object and the human appendage 114.

The processor 1008 can be communicatively coupled with the impact sensor 1400 to receive the one or more output signals from the impact sensor 1400. In embodiments, the processor 1008 is configured to determine that an impact has occurred between the human appendage 114 and the environmental object 300 based at least in part on the one or more output signals from the impact sensor 1400. For example, the impact sensor 1400 can be positioned on or in close proximity to one or more of the human appendage 114 or the environmental object 300, such as by associating the impact sensor 1400 with one or more of the plurality of tags 1002 or the remote reader 1004. In embodiments, the processor 1008 is configured to determine a time of the impact between the human appendage 114 and the environmental object 300 based on the one or more output signals from the impact sensor 1400. For example, the timing device 1200 (e.g., shown in FIG. 12) can be communicatively coupled with the processor 1008, where the processor 1008 can access a time from the timing device 1200 when the one or more output signals from the impact sensor 1400 provide an indication that an impact has occurred between the human appendage 114 and the environmental object 300. In embodiments, the processor 1008 is configured to determine a location of the impact between the human appendage 114 and the environmental object 300 based at least in part on the one or more output signals from the impact sensor 1400. For example, a distinct identity of a tag of the plurality of tags 1002 can be associated with a location of the tag 1002 in the environment. In embodiments, the characteristics of the tags of the plurality of tags 1002 are stored in a memory device (e.g., memory device 1300). By identifying which tag of the plurality of tags 1002 has been impacted, the processor 1008 can determine the location of the impact based on the correlation between the distinct identity and the location of the tags 1002. In embodiments, the processor 1008 is configured to determine a frequency of impacts between the human appendage 114 and the environmental object 300 based on the one or more output signals from the impact sensor 1400. The processor 1008 can determine the frequency of impacts for an operation period of the system 1000, for a specified period of time, for an average time span, or the like. In embodiments, the processor 1008 can determine the time since a previous impact between the human appendage 114 and the environmental object 300 based on the one or more output signals from the impact sensor 1400.

In embodiments, the processor 1008 is configured to determine when a distance between the human appendage 114 and the environmental object 300 is less than the threshold distance based at least in part on the one or more output signals from the impact sensor 1400. The threshold distance can be a predetermined value that corresponds to a safety consideration to prevent or mitigate impact between the human appendage 114 and the environmental object 300. In embodiments, the processor 1008 is configured to determine a time corresponding to when the distance between the human appendage 114 and the environmental object 300 became less than the threshold distance based on the one or more output signals from the impact sensor 1400. For example, the timing device 1200 can be configured to provide a time at which the human appendage 114 and the environmental object 300 came within the threshold distance with respect to each other. In embodiments, the processor 1008 is configured to determine a frequency of instances when the distance between the human appendage 114 and the environmental object 300 became less than the threshold distance based on the one or more output signals from the impact sensor 1400. The processor 1008 can determine the frequency of such instances for an operation period of the system 1000, for a specified period of time, for an average time span, or the like. In embodiments, the processor 1008 can determine the time since a previous instance of when the human appendage 114 and the environmental object 300 came within the threshold distance with respect to each other based on the one or more output signals from the impact sensor 1400.

In embodiments, the memory device 1300 can store data associated with an impact or near impact between the human appendage 114 and the environmental object 300, where a determination of the impact is based at least in part on the one or more output signals from the impact sensor 1400. The data associated with an impact between the human appendage 114 and the environmental object 300 can include, but is not limited to, a time of the impact between the human appendage 114 and the environmental object 300, a location of impact between the human appendage 114 and the environmental object 300, or a frequency of occurrences of impact between the human appendage 114 and the environmental object 300. In embodiments, the memory device 1300 can store data associated with when the distance between the human appendage 114 and the environmental object 300 is less than the threshold distance, where a determination that the distance between the human appendage 114 and the environmental object 300 is less than the threshold distance is based at least in part on the impact sensor 1400. The data associated with when the distance between the human appendage 114 and the environmental object 300 is less than the threshold distance can include, but is not limited to, data associated with when the distance between the human appendage 114 and the environmental object 300 is less than the threshold distance, a location corresponding to when the distance between the human appendage 114 and the environmental object 300 is less than the threshold distance, or a frequency of instances of when the distance between the human appendage 114 and the environmental object 300 is less than the threshold distance.

In embodiments, the processor 1008 is configured to determine that an impact has occurred between the human appendage 114 and the environmental object 300 based on the one or more output signals from the remote reader 1004 and the one or more output signals from the impact sensor 1400. For example, the remote reader 1004 can provide data associated with the proximity of one tag of the plurality of tags 1002 relative to another tag of the plurality of tags 1002, which can provide an indication of when the human appendage 114 is close to or impacted with the environmental object 300. The impact sensor 1400 can be positioned on or in close proximity to one or more of the human appendage 114 or the environmental object 300, such as by associating the impact sensor 1400 with one or more of the plurality of tags 1002 or the remote reader 1004, and can provide data associated with impact to the human appendage 114 or the environmental object 300 depending on where the impact sensor 1400 is located. For example, the impact sensor 1200 can be associated with a tag of the plurality of tags 1002 located on the environmental object 300 and can register an impact to the environmental object 300. The remote reader 1004 can provide supplementary data to determine that the human appendage 114 caused the impact, such as by identifying a proximity of another tag (e.g., a tag coupled to the substrate 1006 located on the human appendage) relative to the impacted tag, where the remote reader 1004 can uniquely identify each tag of the plurality of tags 1002. In embodiments, the processor 1008 is configured to determine a time of the impact between the human appendage 114 and the environmental object 300 based on the one or more output signals from the remote reader 1004 and the one or more output signals from the impact sensor 1400. For example, the timing device 1300 (e.g., shown in FIG. 13) can be communicatively coupled with the processor 1008, where the processor 1008 can access a time from the timing device 1300 when the one or more output signals from the impact sensor 1400 provide an indication that an impact has occurred between the human appendage 114 and the environmental object 300. In embodiments, the processor 1008 is configured to determine a location of the impact between the human appendage 114 and the environmental object 300 based on the one or more output signals from the remote reader 1004 and the one or more output signals from the impact sensor 1400. For example, a distinct identity of a tag of the plurality of tags 1002 can be associated with a location of the tag 1002 in the environment. In embodiments, the characteristics of the tags of the plurality of tags 1002 are stored in a memory device (e.g., memory device 1300). By identifying which tag of the plurality of tags 1002 has been impacted, the processor 1008 can determine the location of the impact based on the correlation between the distinct identity and the location of the tags 1002. In embodiments, the processor 1008 is configured to determine a frequency of impacts between the human appendage 114 and the environmental object 300 based on the one or more output signals from the remote reader 1004 and the one or more output signals from the impact sensor 1400. The processor 1008 can determine the frequency of impacts for an operation period of the system 1000, for a specified period of time, for an average time span, or the like. In embodiments, the processor 1008 can determine the time since a previous impact between the human appendage 114 and the environmental object 300 based on the one or more output signals from the remote reader 1004 and the one or more output signals from the impact sensor 1400.

In embodiments, the processor 1008 is configured to determine when a distance between the human appendage 114 and the environmental object 300 is less than the threshold distance based on the one or more output signals from the remote reader 1004 and the one or more output signals from the impact sensor 1400. The threshold distance can be a predetermined value that corresponds to a safety consideration to prevent or mitigate impact between the human appendage 114 and the environmental object 300. In embodiments, the processor 1008 is configured to determine a time corresponding to when the distance between the human appendage 114 and the environmental object 300 became less than the threshold distance based on the one or more output signals from the remote reader 1004 and the one or more output signals from the impact sensor 1400. For example, the timing device 1200 can be configured to provide a time at which the human appendage 114 and the environmental object 300 came within the threshold distance with respect to each other. In embodiments, the processor 1008 is configured to determine a location of when the distance between the human appendage 114 and the environmental object 300 became less than the threshold distance based on the one or more output signals from the remote reader 1004 and the one or more output signals from the impact sensor 1400. For example, a distinct identity of a tag of the plurality of tags 1002 can be associated with a location of the tag 1002 in the environment. In embodiments, the characteristics of the tags of the plurality of tags 1002 are stored in a memory device (e.g., memory device 1300). By identifying which tag(s) of the plurality of tags 1002 came within a threshold distance of each other, the processor 1008 can determine the location of when the distance between the human appendage 114 and the environmental object 300 became less than the threshold distance based on the correlation between the distinct identity and the location of the tags 1002. In embodiments, the processor 1008 is configured to determine a frequency of instances when the distance between the human appendage 114 and the environmental object 300 became less than the threshold distance based on the one or more output signals from the remote reader 1004 and the one or more output signals from the impact sensor 1400. The processor 1008 can determine the frequency of such instances for an operation period of the system 1000, for a specified period of time, for an average time span, or the like. In embodiments, the processor 1008 can determine the time since a previous instance of when the human appendage 114 and the environmental object 300 came within the threshold distance with respect to each other based on the one or more output signals from the remote reader 1004 and the one or more output signals from the impact sensor 1400.

In embodiments, the memory device 1300 can store data associated with an impact or near impact between the human appendage 114 and the environmental object 300, where a determination of the impact is based on the one or more output signals from the remote reader 1004 and the one or more output signals from the impact sensor 1400. The data associated with an impact between the human appendage 114 and the environmental object 300 can include, but is not limited to, a time of the impact between the human appendage 114 and the environmental object 300, a location of impact between the human appendage 114 and the environmental object 300, or a frequency of occurrences of impact between the human appendage 114 and the environmental object 300. In embodiments, the memory device 1300 can store data associated with when the distance between the human appendage 114 and the environmental object 300 is less than the threshold distance, where a determination that the distance between the human appendage 114 and the environmental object 300 is less than the threshold distance is based on the one or more output signals from the remote reader 1004 and the one or more output signals from the impact sensor 1400. The data associated with when the distance between the human appendage 114 and the environmental object 300 is less than the threshold distance can include, but is not limited to, data associated with when the distance between the human appendage 114 and the environmental object 300 is less than the threshold distance, a location of when the distance between the human appendage 114 and the environmental object 300 is less than the threshold distance, or a frequency of instances of when the distance between the human appendage 114 and the environmental object 300 is less than the threshold distance.

Figure 15:
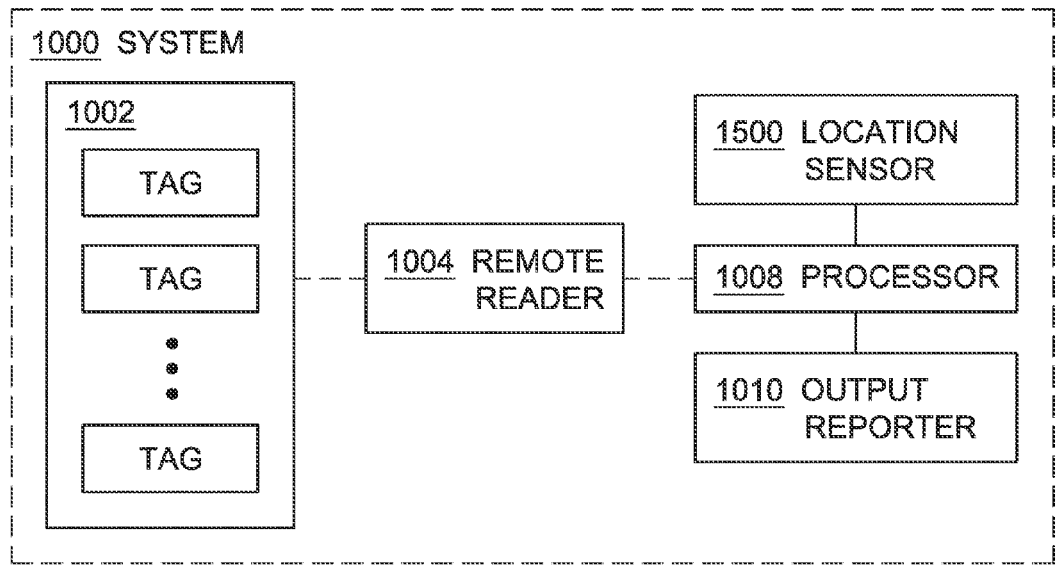
FIG. 15 is a schematic of an embodiment of a system such as shown in FIG. 10.

In embodiments (such as shown in FIG. 15), the system 1000 includes a location sensor 1500 configured to generate one or more output signals associated with a location (e.g., geographical location, absolute location, relative location, etc.) of at least one of the human appendage 114 or the environmental object 300. In embodiments, the location sensor 1500 is configured to determine a location of one or more of the plurality of tags 1002 or the remote reader 1004, which in embodiments can provide an analog for a location of one or more of the human appendage 114 or the environmental object 300. The location sensor 1500 can include, but is not limited to, one or more of a positioning sensor (e.g., a satellite and/or terrestrial-based positioning system, such as a global positioning system, indoor positioning system, a cellular network system, a land mobile radio based system, etc.), an optic sensor (e.g., an imaging device for location recognition), a laser (e.g., laser or laser diode positioning sensors), an acoustic sensor (e.g., acoustic source localization device), or a radar-based sensor (e.g., a frequency modulated continuous wave (FMCW) radar detector/sensor). In embodiments, the location sensor 1500 is configured for positioning on the human appendage 114. For example, the location sensor 1500 can be coupled to the substrate 1006. In embodiments, the location sensor 1500 is positioned remote from at least one of the human appendage 114 or the environmental object 300. For example, the location sensor 1500 can be configured to remotely determine the location of at least one of the human appendage 114 or the environmental object 300. In embodiments, the location sensor 1500 is coupled to the remote reader 1004. For example, the remote reader 1004 can include a location sensor 1500 configured to identify a location of the remote reader 1004, which can correspond to a location of one or more of the human appendage 114 or the environmental object 300 depending on whether the remote reader 1004 is coupled to the substrate 1006, to an environmental object 300, or located remotely elsewhere (e.g., another location within the environment), or which can aid in determining a location of one of more tags of the plurality of tags 1002 (e.g., based on the relative positional differences between the tags 1002 and the remote reader 1004).

In embodiments, the location sensor 1500 includes an accelerometer, which can serve an as initiator for when the location sensor 1500 is operable. For example, the location sensor 1500 can measure one or more of a distance or a direction from an initiation point based on activation of the accelerometer. Such activation can be due to movement of the human appendage 114 (such as when the a tag of the plurality of tags 1002 and the location sensor 1500 are positioned on the substrate 1006 on the human appendage 114), due to impact to the environmental object 300 (such as when a tag of the plurality of tags 1002 and the location sensor 1500 are positioned on either of the human appendage 114 or the environmental object 300), or the like. The initiation point can correspond to one or more of a user reference point (e.g., a position of a user on which the substrate 1006 is coupled), an updatable reference point (e.g., a reference point of the environmental object 300), or the like.

In embodiments, the location sensor 1500 is configured to interact with a network of location beacons to measure the location of at least one of the remote reader 1004 or one or more tags of the plurality of tags 1002. For example, the network of location beacons can include, but is not limited to, beacons configured to periodically or continuously transmit data associated with a location of the respective beacon, beacons configured to periodically or continuously transmit data associated with an operation status of the respective beacon, or the like. The beacons can include devices operating under a common communications standard, including but not limited to, Bluetooth communication protocols, RFID communication protocols, or the like.

The processor 1008 can be communicatively coupled with the location sensor 1500 to receive the one or more output signals from the location sensor 1500. In embodiments, the processor 1008 is configured to determine that an impact has occurred between the human appendage 114 and the environmental object 300 based at least in part on the one or more output signals from the location sensor 1500. For example, the location sensor 1500 can track the location of one or more of the human appendage 114 or the environmental object 300, whereby the processor 1008 can determine that the location of the human appendage 114 or the environmental object 300 overlaps with or substantially matches a location of the other of the human appendage 114 or the environmental object 300. In embodiments, the memory device 1300 stores location information associated with one or more environmental objects 300, where the location sensor 1500 tracks the location of the human appendage 114. The processor 1008 can compare the tracked location of the human appendage 114 to the stored location information associated with one or more environmental objects 300 to determine whether the human appendage 114 impacted with or more of the environmental objects 300. In embodiments, the processor 1008 is configured to determine a time of the impact between the human appendage 114 and the environmental object 300 based at least on the one or more output signals from the location sensor 1500. For example, the timing device 1200 (e.g., shown in FIG. 12)

can be communicatively coupled with the processor 1008, where the processor 1008 can access a time from the timing device 1200 when the one or more output signals from the location sensor 1500 provide an indication that an impact has occurred between the human appendage 114 and the environmental object 300. In embodiments, the processor 1008 is configured to determine a frequency of impacts between the human appendage 114 and the environmental object 300 based on the one or more output signals from the location sensor 1500. The processor 1008 can determine the frequency of impacts for an operation period of the system 1000, for a specified period of time, for an average time span, or the like. In embodiments, the processor 1008 can determine the time since a previous impact between the human appendage 114 and the environmental object 300 based on the one or more output signals from the location sensor 1500.

In embodiments, the processor 1008 is configured to determine when a distance between the human appendage 114 and the environmental object 300 is less than the threshold distance based at least in part on the one or more output signals from the location sensor 1500. The threshold distance can be a predetermined value that corresponds to a safety consideration to prevent or mitigate impact between the human appendage 114 and the environmental object 300. For example, the location sensor 1500 can track the location of one or more of the human appendage 114 or the environmental object 300, whereby the processor 1008 can determine a distance between the human appendage 114 and the environmental object 300, in order to determine that the distance is less than a predetermined threshold distance. In embodiments, the processor 1008 is configured to determine a time corresponding to when the distance between the human appendage 114 and the environmental object 300 became less than the threshold distance based on the one or more output signals from the location sensor 1500. For example, the timing device 1200 can be configured to provide a time at which the human appendage 114 and the environmental object 300 came within the threshold distance with respect to each other. In embodiments, the processor 1008 is configured to determine a frequency of instances when the distance between the human appendage 114 and the environmental object 300 became less than the threshold distance based on the one or more output signals from the location sensor 1500. The processor 1008 can determine the frequency of such instances for an operation period of the system 1000, for a specified period of time, for an average time span, or the like. In embodiments, the processor 1008 can determine the time since a previous instance of when the human appendage 114 and the environmental object 300 came within the threshold distance with respect to each other based on the one or more output signals from the location sensor 1500.

In embodiments, the memory device 1300 can store data associated with an impact or near impact between the human appendage 114 and the environmental object 300, where a determination of the impact is based at least in part on the one or more output signals from the location sensor 1500. The data associated with an impact between the human appendage 114 and the environmental object 300 can include, but is not limited to, a time of the impact between the human appendage 114 and the environmental object 300, a location of impact between the human appendage 114 and the environmental object 300, or a frequency of occurrences of impact between the human appendage 114 and the environmental object 300. In embodiments, the memory device 1300 can store data associated with when the distance between the human appendage 114 and the environmental object 300 is less than the threshold distance, where a determination that the distance between the human appendage 114 and the environmental object 300 is less than the threshold distance is based at least in part on the location sensor 1500. The data associated with when the distance between the human appendage 114 and the environmental object 300 is less than the threshold distance can include, but is not limited to, data associated with when the distance between the human appendage 114 and the environmental object 300 is less than the threshold distance, a location of when the distance between the human appendage 114 and the environmental object 300 is less than the threshold distance, or a frequency of instances of when the distance between the human appendage 114 and the environmental object 300 is less than the threshold distance.

Figure 16:
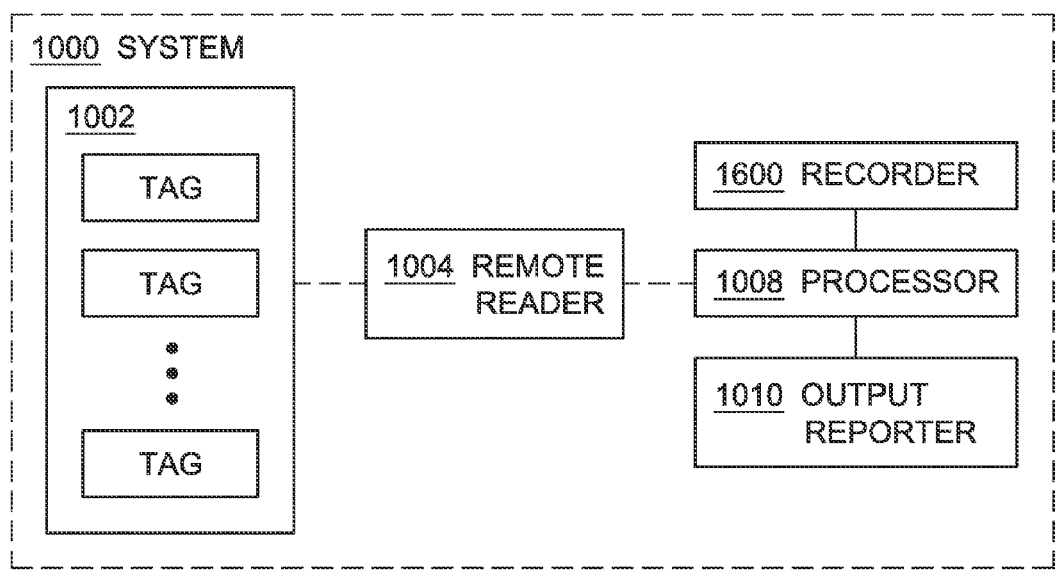
FIG. 16 is a schematic of an embodiment of a system such as shown in FIG. 10.

In embodiments (such as shown in FIG. 16), the system 1000 can include a recorder 1600 operably coupled to the processor 1008. In general, the recorder 1600 is configured to record, store, or the like, data, output signals, and communication signals generated by one or more components of the system 1000. For example, the recorder 1600 can be configured to record the one or more output signals from the remote reader 1004 in a memory device, such as the memory device 1300. In embodiments, the recorder 1600 is configured to store in the memory device 1300 data associated with an impact between the human appendage 114 and the environmental object 300. Such data can include, but is not limited to, a time of impact, a location of impact, or a frequency of impact. In embodiments, the recorder 1600 is configured to store in the memory device 1300 data associated with when the distance between the human appendage 114 and the environmental object 300 is less than the threshold distance. Such data can include, but is not limited to, a time corresponding to when the distance between the human appendage 114 and the environmental object 300 is less than the threshold distance, a location corresponding to when the distance between the human appendage 114 and the environmental object 300 is less than the threshold distance, or a frequency of instances of when the distance between the human appendage 114 and the environmental object 300 is less than the threshold distance.

In embodiments, the processor 1008 can be configured to make determinations regarding one or more physical aspects associated with at least one of the human appendage 114 and the environmental object 300. For example, the processor 1008 can be configured to determine a force of an impact between the human appendage 114 and the environmental object 300. The processor 1008 can access data from one or more sensors of the system 1000 to make such determinations. For example, the processor 1008 can access data from a force sensor, from a pressure sensor, from an accelerometer, or the like. In embodiments, the processor 1008 is configured to determine what a force of a potential impact would be, should such potential impact actually occur. For example, the processor 1008 can determine, based on at least a current or previous velocity, speed, or the like of the human appendage 114, what force the human appendage 114 would impact the environmental object 300 should the human appendage 114 and the environmental object 300 actually collide. In embodiments, the processor 1008 can extrapolate and/or interpolate one or more of positional data, speed data, velocity data, or acceleration data to estimate or predict the force at which the human appendage 114 and the environmental object 300 would collide.

The output reporter 1010 is configured to generate one or more communication signals to report information associated with operation of the system 1000. In embodiments, the output reporter 1010 is configured to generate one or more communication signals responsive to instruction by the processor 1008. In embodiments, the output reporter 1010 can correspond to the output reporter 110 described herein, including but not limited to the structural and functional characteristics thereof. For example, the information from the output reporter 1010 may be provided one or more of visually (e.g., via transmission or display of visual information), audibly (e.g., via transmission or display of auditory information), tactually (e.g., via presentation of tactile information), or as data (e.g., via transmission or display of one or more data signals associated with the information to convey). The output reporter 1010 can function in combination with the processor 1008 to provide visual, auditory, or tactile information associated with the human appendage 114 and/or the environmental object 300, such as the proximity of the human appendage 114 with respect to the environmental object 300, impact information, threshold information, or the like.

In embodiments, the output reporter 1010 generates (e.g., via the display device 900) a graphical representation of data associated with operation of the system 1000. The graphical representation can include a map-based display of the information, which can provide the data with respect to absolute or relative locations. The map can correspond to a region proximate one or more environmental objects 300 and can display information associated with interaction between the human appendage 114 and the one or more environmental objects 300. For example, the map can indicate frequency of impact (or near impact) between the human appendage 114 and various environmental objects 300 where the data is color-coded to differentiate between differing frequencies. Other presentations of data are possible, including but not limited to, topographical plots, bar plots, pie plots, or the like. As another example, the map can indicate time of impact (or near impact) between the human appendage 114 and various environmental objects 300 where the data is coded to differentiate between differing times of impact (or near impact).

In embodiments, the processor 1008 is configured to generate a recommendation based on one or more output signals from one or more of the remote reader 1004, the impact sensor 1400, or the location sensor 1500. The recommendation can include, but is not limited to, a recommendation pertaining to the environmental object 300, where such recommendation can reduce at least one of a likelihood of impact with the environmental object 300 or a degree of severity of impact with the environmental object 300. For example, in embodiments, the recommendation includes a recommendation to reposition the environmental object 300 to a new location within the environment. The new location within the environment can be a location that an individual is less likely to impact with the environmental object 300 as compared to the previous location (i.e., the location prior to the recommendation to reposition the environmental object 300). For example, the processor 1008 can access (e.g., from the memory device 1300) one or more modules configured to analyze the positioning of the environmental object 300 based on one or more output signals from one or more of the remote reader 1004, the impact sensor 1400, or the location sensor 1500. Where the processor 1008 determines that the current position of the environmental object 300 results in too many impacts (e.g., the number of impacts between the human appendage 114 and the environmental object 300 exceeds a threshold impact value), the processor 1008 can generate the recommendation to reposition the environmental object 300 to a new location within the environment. The new location within the environment can include one or more of a different location within the environment than the previous position prior to the recommendation to reposition the environmental object 300, a location within a threshold distance from the previous position, a location outside of a threshold distance from the previous position, a location determined to have a probability of fewer impacts between the human appendage 114 and the environmental object 300, or so forth. In embodiments, the processor 1008 conveys the recommendation to reposition the environmental object 300 via the output reporter 1010. For example, the output reporter 1010 can generate one or more of a visual indication of the recommendation (e.g., via the display device 900), an audible indication of the recommendation (e.g., via the audio device 902), a tactile indication of the recommendation (e.g., via the tactile device 904), a physical indication of the recommendation (e.g., via the printing device 906), or a transmitted indication via one or more data signals (e.g., via the transmitter 908).

In embodiments, the processor 1008 is configured to generate a visible recommendation associated with a map corresponding to a region proximate the environmental object 300. The processor 1008 can generate the map via the output reporter 1010 to provide the visible recommendation. The map can include information including but not limited to, a recommended location to reposition the environmental object 300, a listing of areas proximate the environmental object 300 within the environment to which the environmental object 300 can be repositioned, a region proximate the environmental object 300 within a threshold distance, a region corresponding to locations outside of a threshold distance from the environmental object 300, data associated with impact frequency associated with one or more environmental objects, or so forth. For example, in embodiments, the processor 1008 generates the map via the output reporter 1010, wherein the map provides a visual distinction between varying intensities of impact between respective environmental objects (e.g., lower wavelength colors for areas corresponding to more impacts, higher wavelength colors for areas corresponding to fewer impacts, etc.).

In embodiments, the recommendation generated by the processor 1008 includes a recommendation to provide the environmental object 300 with a cushioning material. The cushioning material can reduce a degree of severity of impact with the environmental object 300 by absorbing or mitigating at least a portion of the force of impact between the human appendage 114 and the environmental object 300. For example, cushioning material can include, but is not limited to, fibrous materials (e.g., synthetic fibers, fabric, felt, paper, cardboard, feather, etc.), polymeric materials (e.g., foam, memory foam, rubber, polystyrene, polypropylene, polyethylene, polyurethane, etc.), entrapped gas material (e.g., air cushions, gas enclosed within plastic film, etc.), mechanical devices (e.g., shock absorber, spring-based device, pneumatic device, etc.), or the like. The processor 1008 can access (e.g., from the memory device 1300) one or more modules configured to analyze force of impacts between the environmental object 300 and another object (e.g., the human appendage 114) based on one or more output signals from one or more of the remote reader 1004, the impact sensor 1400, or the location sensor 1500. In embodiments, when the processor 1008 determines that one or more impacts with the environmental object 300 results in a force of impact that exceeds a threshold force of impact value, the processor 1008 can generate the recommendation to provide the environmental object 300 with a cushioning material to reduce or mitigate the force of subsequent impacts with the environmental object 300. In embodiments, the processor 1008 conveys the recommendation to provide the cushioning material to the environmental object 300 via the output reporter 1010. For example, the output reporter 1010 can generate one or more of a visual indication of the recommendation (e.g., via the display device 900), an audible indication of the recommendation (e.g., via the audio device 902), a tactile indication of the recommendation (e.g., via the tactile device 904), a physical indication of the recommendation (e.g., via the printing device 906), or a transmitted indication via one or more data signals (e.g., via the transmitter 908).

In embodiments, the recommendation generated by the processor 1008 includes a recommendation to provide the environmental object 300 with a visible indicator. The visible indicator can reduce the likelihood of impact between the human appendage 114 and the environmental object 300 by providing a visual indication associated with the position of the environmental object 300 within the environment. For example, the visual indicator can include a visible light source that can be placed on/near the environmental object 300 to provide an individual with a visual indication associated with the position of the environmental object 300 within the environment. The visible light source can illuminate at least a portion of the environmental object 300, which can assist an individual in viewing the environmental object 300, such as during periods of darkness within the environment (e.g., nighttime, power failure, etc.). In embodiments, the processor 1008 is configured to activate the visual indicator based upon one or more output signals from one or more of the remote reader 1004, the impact sensor 1400, or the location sensor 1500. For example, the output signals from one or more of the remote reader 1004, the impact sensor 1400, or the location sensor 1500 can provide an indication that the human appendage 114 is within a threshold distance from the environmental object 300, whereby the processor 1008 activates the visual indicator to provide a warning to the individual regarding a potential impact with the environmental object 300.

In embodiments, the recommendation generated by the processor 1008 includes a recommendation to provide the environmental object 300 with an audible indicator. The audible indicator can reduce the likelihood of impact between the human appendage 114 and the environmental object 300 by providing an auditory indication associated with the position of the environmental object 300 within the environment. For example, the audible indicator can include an alarm device or speaker device that can be placed on/near the environmental object 300 to provide an individual with an auditory indication associated with the position of the environmental object 300 within the environment. The audible indicator can alert an individual to the presence of the environmental object 300, which can assist an individual in avoiding contact or impact with the environmental object 300, such as during periods of darkness within the environment (e.g., nighttime, power failure, etc.), for individuals with visual impairments, or the like. In embodiments, the processor 1008 is configured to activate the audible indicator based upon one or more output signals from one or more of the remote reader 1004, the impact sensor 1400, or the location sensor 1500. For example, the output signals from one or more of the remote reader 1004, the impact sensor 1400, or the location sensor 1500 can provide an indication that the human appendage 114 is within a threshold distance from the environmental object 300, whereby the processor 1008 activates the audible indicator to provide a warning to the individual regarding a potential impact with the environmental object 300.

In embodiments, the output reporter 1010 is configured to generate an alert responsive to instruction by the processor 1008 when a distance between the human appendage 114 and the environmental object 300 is less than a threshold distance. The environmental object 300 can be identified by the system 1000 as at least one of a risk for impact with the human appendage 114 or a previously impacted object (e.g., previously impact by the human appendage 114, another environmental object, etc.). For example, the processor 1008 can access (e.g., from the memory device 1300) one or more modules configured to analyze a position of a particular environmental object 300 (or an analog for the environmental object, such as a tag of the plurality of tags 1002, the remote reader 1004, etc.) relative to the human appendage 114 (or an analog for the human appendage 114, such as a tag of the plurality of tags 1002, the remote reader 1004, etc.) based at least in part on one or more output signals from one or more of the remote reader 1004, the impact sensor 1400, or the location sensor 1500 to determine a distance between the human appendage 114 and the environmental object 300. The processor 1008 can then compare the determined distance between the human appendage 114 and the environmental object 300 to a threshold distance to determine whether the determined distance is less than the threshold distance. The threshold distance can be a stored value that can depend on spacing considerations (e.g., constraints of the size of the environment), can depend on particular environmental objects (e.g., more dangerous environmental objects can have a larger attributed threshold distance), or the like. Such comparison can occur on a periodic basis, a continuous basis, or the like. Where the processor 1008 determines that the distance between the environmental object 300 and the human appendage 114 is less than the threshold distance, the processor 1008 can instruct the output reporter 1010 to generate an alert. In embodiments, the alert can be one or more of an audible alert, a visual alert, or a tactile alert.

In embodiments, the alert is associated with the human appendage 114. An alert associated with the human appendage 114 can include, but is not limited to, one or more of an alert displayed on the human appendage 114, an alert projected to the human appendage 114 (e.g., from a location remote from the human appendage 114), an alert indicating the human appendage 114, or the like. For example, the alert can include, but is not limited to, an alert originating from a device on the human appendage 114, an alert indicating or identifying the human appendage 114 (e.g., displaying the alert on a screen that provides at least an indication of the human appendage 114, such as by accentuating an area, region, object, etc. on a map), a visual or audible alert projected from a device onto the human appendage 114 (e.g., directing light or sound at the human appendage 114), or the like. In embodiments, the alert is associated with the environmental object 300. An alert associated with the environmental object 300 can include, but is not limited to, one or more of an alert displayed on the environmental object 300, an alert projected to the environmental object 300 (e.g., from a location remote from the environmental object 300), an alert indicating the environmental object 300, or the like. For example, the alert can include, but is not limited to, an alert originating from a device on the environmental object 300, an alert indicating or identifying the environmental object 300 (e.g., displaying the alert on a screen that provides at least an indication of the environmental object 300, such as by accentuating an area, region, object, etc. on a map), a visual or audible alert projected from a device onto environmental object 300 (e.g., directing light or sound at the environmental object 300), or the like.

Figure 17:
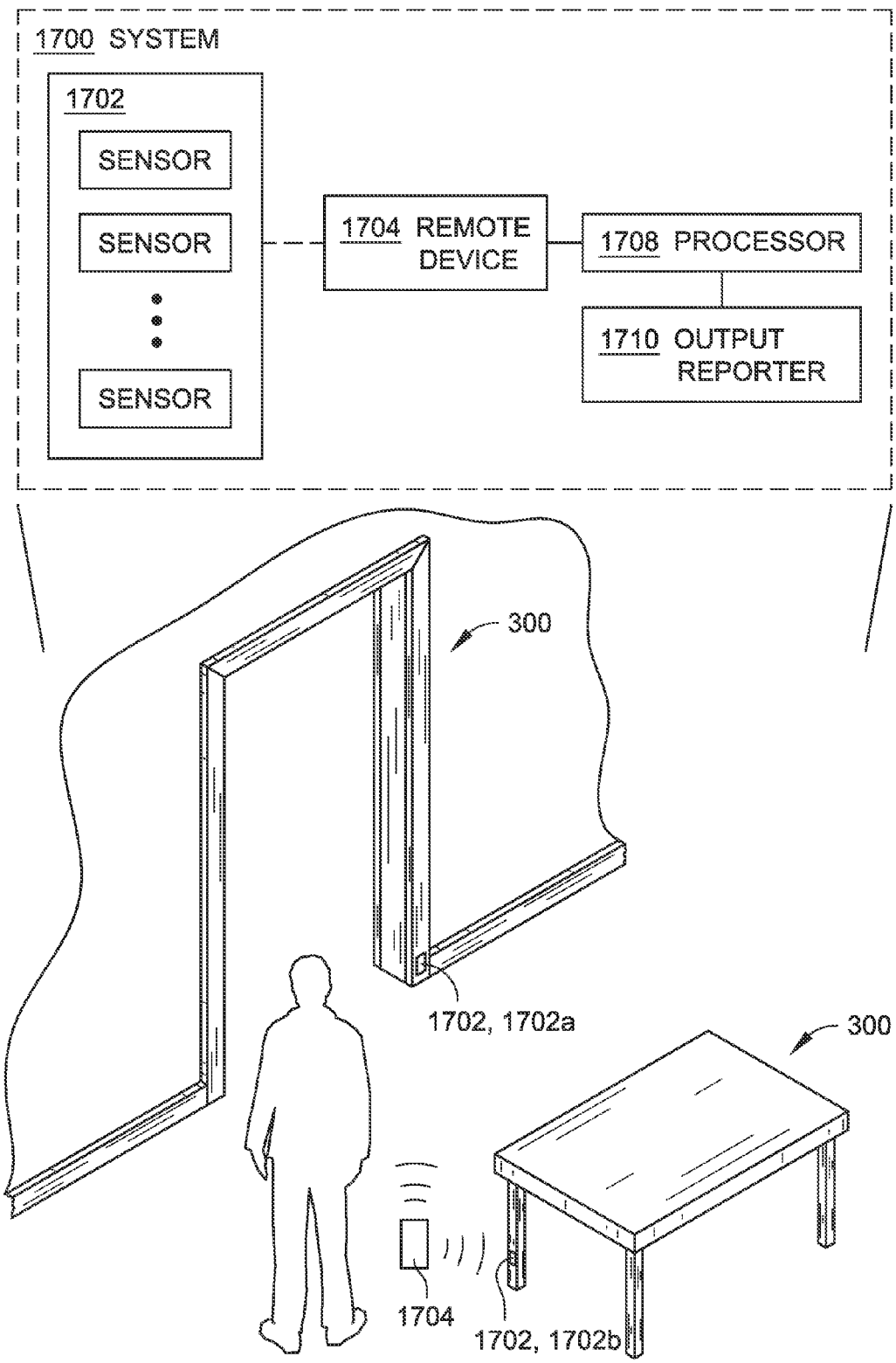
FIG. 17 is a schematic of a system with interactive management of environmental objects relative to human appendages.
Figure 18:
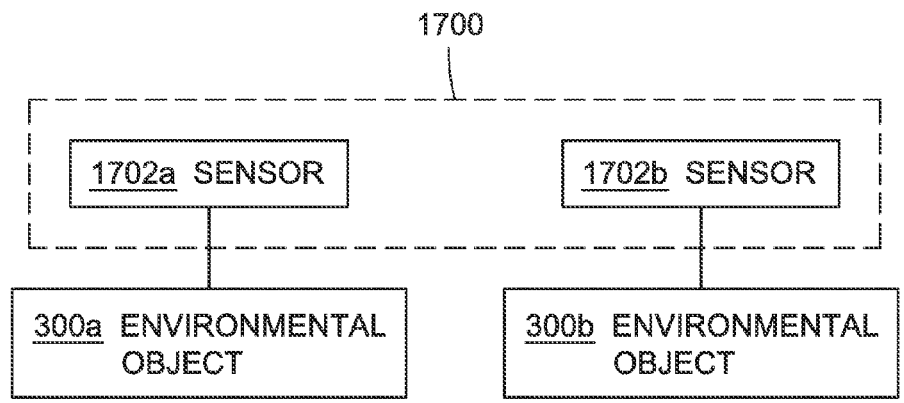
FIG. 18 is a schematic of an embodiment of a system such as shown in FIG. 17.

In embodiments, as shown in FIG. 17, a system 1700 is configured to monitor an environment through which an individual can move, where the system can identify environmental objects in proximity to an appendage of the individual and/or in proximity to other environmental objects to aid in preventing damage to the individual associated with physical impact between the environmental object and the appendage. The system 1700 includes a plurality of sensors 1702, a remote device 1704, a processor 1708, and an output reporter 1710. In general, each sensor of the plurality of sensors 1702 is configured for positioning proximate a respective environmental object 300 of a plurality of environmental objects 300 for monitoring characteristics (e.g., physical characteristics) associated with the respective environmental objects 300. For example, as shown in FIG. 18, the plurality of sensors 1702 can include a first sensor 1702a configured to be coupled to a first environmental object 300a and a second sensor 1702b configured to be coupled to a second environmental object 300b. While two sensors 1702 and two environmental objects 300 are shown, the system 1700 is not limited to two sensors 1702 and two environmental objects 300, and can, for example, include three or more sensors 1702 and three or more environmental objects 300. The sensors of the plurality of sensors 1702 can include, but are not limited to, at least one proximity sensor, at least one pressure sensor, at least one accelerometer, or so forth. For example, the proximity sensor can include one or more of an optical proximity sensor, an acoustic proximity sensor, or an electromagnetic proximity sensor. The optical proximity sensor, the acoustic proximity sensor, and the electromagnetic proximity sensor can be configured to emit signals and detect reflected signals in accordance with their specific detection protocols. An optical proximity sensor can detect one or more optical signals (e.g., one or more optical electromagnetic signals) and generate one or more sense signals in response thereto. For example, an optical proximity sensor of the plurality of sensors 1702 can be configured to detect and/or identify an environmental object 300 and/or a human appendage 114, and their proximity relative to components of the system 1700 based on detected optical signals. The optical sensor can include, but is not limited to, a photodetector (e.g., to detect one or more electromagnetic signals reflected from a surface of an object), an imaging device (e.g., a camera to generate a visual image of one or more objects in proximity to components of the system 1700), or the like. For example, an optical proximity sensor of the plurality of sensors 1702 can be configured to emit a light signal and detect a reflected light signal, for example a reflected light signal that is reflected by an environmental object 300 and/or a human appendage 114. The acoustic proximity sensor can detect and/or identify objects and their proximity relative to components of the system 1700 based on detected acoustic signals. For example, an acoustic proximity sensor of the plurality of sensors 1702 can be configured to detect and/or identify an environmental object 300 and/or a human appendage 114, and their proximity relative to components of the system 1700 based on detected acoustic signals. For example, an acoustic proximity sensor of the plurality of sensors 1702 can be configured to emit an acoustic signal and detect a reflected signal, for example a reflected acoustic signal that is reflected by an environmental object 300 and/or a human appendage 114. The acoustic proximity sensor can include, but is not limited to, sensors configured to detect ultrasonic signals, radio-frequency signals, or the like. An electromagnetic proximity sensor can detect and/or identify objects and their proximity relative to components of the system 1700 based on detected electromagnetic signals. For example, an electromagnetic proximity sensor of the plurality of sensors 1702 can be configured to detect and/or identify an environmental object 300 and/or a human appendage 114, and their proximity relative to components of the system 1700 based on detected electromagnetic signals. For example, an electromagnetic proximity sensor of the plurality of sensors 1702 can be configured to emit an electromagnetic signal and detect a reflected electromagnetic signal, for example a reflected electromagnetic signal that is reflected by an environmental object 300 and/or a human appendage 114. The electromagnetic proximity sensor can include, for example, a bolometer or a thermal imaging device (e.g., to measure incident electromagnetic radiation of objects in proximity to components of the system 100). In embodiments, the sensors of the plurality of sensors 1702 are configured to generate one or more output signals corresponding to at least one of a proximity of the human appendage 114 with the respective sensor of the plurality of sensors 1702 or an impact between the human appendage and the respective environmental object 300.

The remote device 1704 is positioned remotely from, and communicatively coupled to, the plurality of sensors 1702. In embodiments, the remote device 1704 is configured to distinctly identify each sensor of the plurality of sensors 1702 and to receive one or more output signals from each sensor of the plurality of sensors 1702. For example, the remote device 1704 can include one or more transmitters, receivers, transceivers, or the like configured to transmit data between the remote device 1704 and the plurality of sensors 1702. In embodiments, the remote device is configured to distinctly identify each of the plurality of sensors 1702 based on a unique identifier attributable to each sensor of the plurality of sensors 1702. The unique identifier can include information associated with one or more of the respective sensor or the environmental object on which the respective sensor is positioned. For example, the unique identifier can include information associated with, but not limited to, a previously-impacted object, a particular object (e.g., differentiating between different objects within the environment, such as the door jamb (labeled 1702a) and the table (labeled 1702b) shown in FIG. 17), a particular feature or characteristic(s) of an environmental object (e.g., a characterization of a soft environmental object differentiated from a characterization of a hard environmental object, etc.), a prioritization of environmental objects 300 (e.g., disregarding output signals associated with impact or near impact with one environmental object, while prioritizing output signals associated with impact or near impact with a prioritized environmental object), or so forth. In embodiments, the remote device 1704 is configured to distinctly identify each of the plurality of sensors 1702 based on the unique identifier and a location of each of the plurality of sensors 1702 stored in memory corresponding to the unique identifier. A memory device (e.g., memory device 500, memory device 1300, a different memory device, etc.) can have data stored thereon associating a location of a sensor (which can correspond to a location of an environmental object 300 on which the sensor is positioned) with a unique identifier of the sensor. For example, a memory device can have data stored thereon associating a location of the sensor 1702a on the door jamb with the unique identifier of the sensor 1702a on the door jamb, and can have data stored thereon associating a location of the sensor 1702b on the table with the unique identifier of the sensor 1702b on the table. Such association of location and unique identifiers can facilitate determination of where impacts or near misses occur, what environmental objects have been impacted or nearly impacted based on location information, or so forth. In embodiments, the remote device 1704 is configured to distinctly identify each of the plurality of sensors 1702 based on a location of each sensor of the plurality of sensors 1702. In embodiments, the remote device 1704 is configured to distinctly identify each of the plurality of sensors 1702 based on the one or more output signals from each sensor of the plurality of sensors 1702. For example, the sensors of the plurality of sensors 1702 can include identifying information (e.g., a unique identifier) included in the one or more output signals such that the remote device 1704 can distinctly identify each sensor based on the identifying information included in the one or more output signals.

In embodiments, the sensors of the plurality of sensors 1702 are configured to passively transmit the one or more output signals. The passive transmission of the one or more output signals can be received by the remote device 1704, such as on a continuous basis, a periodic basis, or the like. For example, the sensors of the plurality of sensors 1702 can transmit the one or more output signals according to a unit interval (e.g., every millisecond, every second, every ten seconds, every thirty seconds, every minute, every hour, etc.). The remote device 1704 can receive the one or more output signals based on the unit interval, where if an output signal is not received from a particular sensor, the remote device 1704 can provide an indication regarding the failure to receive such output signals. Such an indication can result from a malfunction of a particular sensor, from an impact to the particular sensor, a power status of the particular sensor, or the like.

In embodiments, the sensors of the plurality of sensors 1702 are configured to actively transmit the one or more output signals responsive to a request from the remote device 1704. For example, the remote device 1704 can transmit a request signal to one or more sensors of the plurality of sensors 1702 to generate and/or transmit the one or more output signals. The request signal can be tailored to a particular sensor of the plurality of sensors 1702, such as by utilizing the unique identifier associated with the particular sensor. Alternatively, the request signal can be generally broadcast to the plurality of sensors 1702 for generalized instruction for the plurality of sensors to generate and/or transmit the one or more output signals. The transmission of the request signal can be facilitated by a transmitter, a transceiver, or the like coupled to or integrated with the remote device 1704. In embodiments, the sensors of the plurality of sensors 1702 are configured to actively transmit the one or more output signals only upon detection of at least one of the proximity of the human appendage 114 with the sensor is less than a threshold proximity or an impact between the human appendage 114 and the respective environmental object 300. For example, the remote device 1704 can transmit the request signal to one or more sensors of the plurality of sensors 1702, where the sensors of the plurality of sensors 1702 include control programming operable to generate and/or transmit the one or more output signals only upon detection of at least one of the proximity of the human appendage 114 with the sensor is less than a threshold proximity or an impact between the human appendage 114 and the respective environmental object 300. Thus, in these embodiments, only sensors registering an impact or a near impact would actively respond to the request from the remote device 1704. In embodiments, only sensors registering an impact would actively respond to the request from the remote device 1704. In embodiments, only sensors registering a near impact (e.g., upon detection of the proximity of the human appendage 114 with the sensor is less than the threshold proximity) would actively respond to the request from the remote device 1704.

In embodiments, the sensors of the plurality of sensors 1702 are configured to transmit the one or more output signals only upon detection of at least one of the proximity of the human appendage 114 with the sensor is less than a threshold proximity or an impact between the human appendage 114 and the respective environmental object 300 (e.g., the environmental object on which the respective sensor of the plurality of sensors 1702 is positioned). The remote device 1702 can passively monitor for any output signals from sensors that transmit. For example, the sensors of the plurality of sensors 1702 can monitor the environment proximate to the respective environmental object 300 on which respective sensors of the plurality of sensors are positioned. When an impact to the environmental object 300 is detected by a respective sensor, or when a human appendage 114 is detected by a respective sensor, where the human appendage 114 is located at a distance from the sensor that is less than the threshold distance, the respective sensor of the plurality of sensors 1702 can then transmit the one or more output signals (e.g., for receipt by the remote device 1704). In embodiments, only sensors registering an impact would transmit the one or more output signals. In embodiments, only sensors registering a near impact (e.g., upon detection of the proximity of the human appendage 114 with the sensor is less than the threshold proximity) would transmit the one or more output signals. In embodiments, the remote device 1704 is configured to distinctly identify a source sensor of the one or more output signals based upon a unique identifier attributable to each sensor of the plurality of sensors 1702. For example, the one or more output signals from the sensors of the plurality of sensors 1702 can include a unique identifier attributable to each sensor, where the remote device 1704 can identify the unique identifier to identify the source sensor of the one or more output signals (e.g., upon transmission by the sensors when an impact or near impact is detected). In embodiments, the remote device 1704 is configured to distinctly identify each of the plurality of sensors 1702 based on the unique identifier and a location of each of the plurality of sensors 1702 stored in memory corresponding to the unique identifier. In embodiments, each sensor of the plurality of sensors 1702 is configured to transmit the one or more output signals on at least an interval basis (e.g., a transmission unit interval), and wherein only impacted sensors of the plurality of sensors 1702 are configured to transmit the one or more output signals corresponding to an impact between the human appendage 114 and the respective environmental object 300 upon impact.

The processor 1708 is operably coupled to the remote device 1704 and is configured to process the one or more output signals associated with the plurality of sensors 1702. Based on the processing of the one or more output signals from a sensor, the processor 1708 is configured to provide an indication of at least one of the proximity of the human appendage with the sensor or when an impact between the human appendage 114 and the respective environmental object 300 occurs based on a threshold value being exceeded. In embodiments, the processor 1708 is configured to process the one or more output signals to determine which sensor of the plurality of sensors 1702 at least one of incurred an impact or incurred a proximity to the human appendage less than a threshold proximity. For example, the processor 1708 can determine which sensor of the plurality of sensors 1702 at least one of incurred an impact or incurred a proximity to the human appendage less than a threshold proximity based on one or more of a unique identifier associated with the sensor, a location of an origin of the one or more output signals, or the like. In embodiments, the processor 1708 generates one or more data signals associated with the indication for reporting via the output reporter 1710. The processor 1708 and the remote device 1704 can communicate via wired or wireless communication protocols such that the processor 1708 receives the one or more output signals from the remote device 1704. For example, the processor 1708 can be positioned remotely from the remote device 1704, positioned adjacent to the remote device 1704, coupled to the remote device 1704, or the like.

In embodiments, the processor 1708 can correspond to one or more of the processor 108 or the processor 1008 described herein, including but not limited to the structural and functional characteristics thereof. The processor 1708 includes components to process the one or more output signals from the remote device 1704 and to provide instruction to the output reporter 1710 to generate one or more communication signals associated with one or more of data associated with the one or more output signals or determinations made by the processor 1708. For example, the processor 1708 can include a microprocessor, a central processing unit (CPU), a digital signal processor (DSP), an application-specific integrated circuit (ASIC), a field programmable gate entry (FPGA), or the like, or any combinations thereof, and can include discrete digital or analog circuit elements or electronics, or combinations thereof. In one embodiment, the computing device includes one or more ASICs having a plurality of predefined logic components. In one embodiment, the computing device includes one or more FPGAs having a plurality of programmable logic commands.

In embodiments, the processor 1708 is configured to determine whether an impact has occurred between the human appendage 114 and the respective environmental object 300 based on the one or more output signals. For example, the sensor 1702b associated with the table in FIG. 17 can generate one or more output signals when disrupted by the individual in the room (e.g., impacted by a leg of the individual), where the remote device 1704 can distinctly identify the sensor 1702b and transmit the one or more output signals for processing by the processor 1708. In embodiments, the processor 1708 compares the data associated with the one or more output signals with reference data indicative of an impact to determine when an impact occurs between the sensor 1702b and the human appendage 114. For example, the reference data indicative of an impact (or a comparison module having the reference data included) can be stored in a memory device for retrieval by the processor 1708 for comparison to the one or more output signals to determine when an impact occurs.

Figure 19:
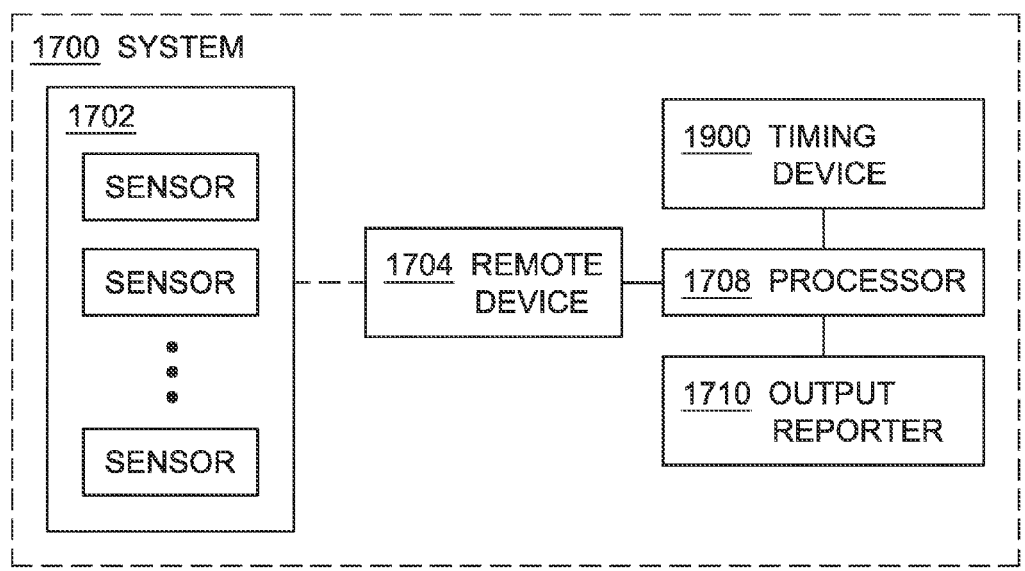
FIG. 19 is a schematic of an embodiment of a system such as shown in FIG. 17.

In embodiments, the processor 1708 is configured to determine a time of the impact between the human appendage 114 and the respective environmental object 300 based on the one or more output signals from the plurality of sensors 1702. For example, as provided in FIG. 19, the system 1700 can include a timing device 1900 communicatively coupled with the processor 1708 and configured to provide a time at which the human appendage 114 and the respective environmental object 300 impact each other. In embodiments, the timing device 1900 can correspond to one or more of the timing device 400 or the timing device 1200 described herein, including but not limited to the structural and functional characteristics thereof. For example, the timing device 1900 can include, but is not limited to a mechanical timing device, an electromechanical timing device, an electrical timing device, a programmable logic controller, a hardware timing device, or the like. In embodiments, the processor 1708 is configured to determine a location of the impact based on the one or more output signals and on a distinct identity of at least one sensor of the plurality of sensors 1702. For example, the distinct identity can provide provided a unique identifier recognizable by the remote device 1704 and/or the processor 1708 and included in the one or more output signals. The location of the impact can be determined, for example, by retrieving a location stored in a memory that is associated with the distinct identity of the sensor (e.g., a distinct identity of the sensor 1702a is associated with a location corresponding to the doorjamb, such as a geographical location, absolute location, relative location, descriptive location, etc.). In embodiments, the processor 1708 is configured to determine a frequency of impacts between the human appendage 114 and the respective environmental object 300 based on the one or more output signals from the plurality of sensors 1702. The processor 1708 can determine the frequency of impacts for an operation period of the system 1700, for a specified period of time, for an average time span, or the like. In embodiments, the processor 1708 can determine the time since a previous impact between the human appendage 114 and the respective environmental object 300 based on the one or more output signals from the plurality of sensors 1702.

In embodiments, the processor 1708 is configured to determine when a distance between the human appendage 114 and the respective environmental object 300 is less than the threshold distance based on the one or more output signals from the plurality of sensors 1702. Such determination can provide an indication that the human appendage 114 and the respective environmental object 300 are within sufficient proximity to pose a threat for impact with one another, or missed impacting each other by a margin that is less than the threshold distance (e.g., a near impact). For example, an interaction or impact with a sensor of the plurality of sensors 1702 that is coupled to the respective environmental object 300 can be used as a proxy for determining that a human appendage 114 and the respective environmental object 300 are at a distance from each other that is less than the threshold distance. The interaction between the sensor and the human appendage can include a distance measurement by the sensor to determine a distance from the sensor to the human appendage. The threshold distance can be a predetermined value that corresponds to a safety consideration to prevent or mitigate impact between the human appendage 114 and the respective environmental object 300. In embodiments, the processor 1708 is configured to determine a time corresponding to when the distance between the human appendage 114 and the respective environmental object 300 became less than the threshold distance based on the one or more output signals from the plurality of sensors 1702. The timing device 1900 can be configured to provide a time at which the human appendage 114 and the environmental object 300 came within the threshold distance with respect to each other. For example, when the processor 1708 determines that the human appendage 114 and the environmental object 300 are within the threshold distance with respect to each other, the processor 1708 can refer to the timing device 1900 to receive the current time from the timing device 1900. In embodiments, the processor 1708 is configured to determine a location corresponding to where the distance between the human appendage 114 and the respective environmental object 300 became less than the threshold distance based on the one or more output signals. For example, the location can correspond to a location of a sensor that generates one or more output signals indicating a near impact with the human appendage 114. In embodiments, the processor 1708 is configured to determine a location corresponding to where the distance between the human appendage 114 and the respective environmental object 300 became less than the threshold distance based on the one or more output and on a distinct identity of at least one sensor of the plurality of sensors 1702. For example, the distinct identity can provide provided a unique identifier recognizable by the remote device 1704 and/or the processor 1708 and included in the one or more output signals. The location of the sensor registering a near impact can be determined, for example, by retrieving a location stored in a memory that is associated with the distinct identity of the sensor (e.g., a distinct identity of the sensor 1702*a* is associated with a location corresponding to the doorjamb, such as a geographical location, absolute location, relative location, descriptive location, etc.). In embodiments, the processor 1708 is configured to determine a frequency of instances when the distance between the human appendage 114 and the respective environmental object 300 became less than the threshold distance based on the one or more output signals from the plurality of sensors 1702. The processor 1708 can determine the frequency of such instances for an operation period of the system 1000, for a specified period of time, for an average time span, or the like. In embodiments, the processor 1708 can determine the time since a previous instance of when the human appendage 114 and the respective environmental object 300 came within the threshold distance with respect to each other based on the one or more output signals from the plurality of sensors 1702.

In embodiments, the sensors of the plurality of sensors 1702 are arranged as a sensor array, where each sensor of the plurality of sensors 1702 is positioned in a unique location within the sensor array. The unique location of each sensor within the senor array can be identified based on the one or more output signals from the plurality of sensors 1702, such as when the one or more output signals include a unique identifier attributable to respective sensors of the plurality of sensors 1702. In embodiments, the processor 1708 is configured to determine a location of an impact between the human appendage 114 and the respective environmental object 300 based at least in part on one or more output signals from respective sensors within the sensor array.

Figure 20:
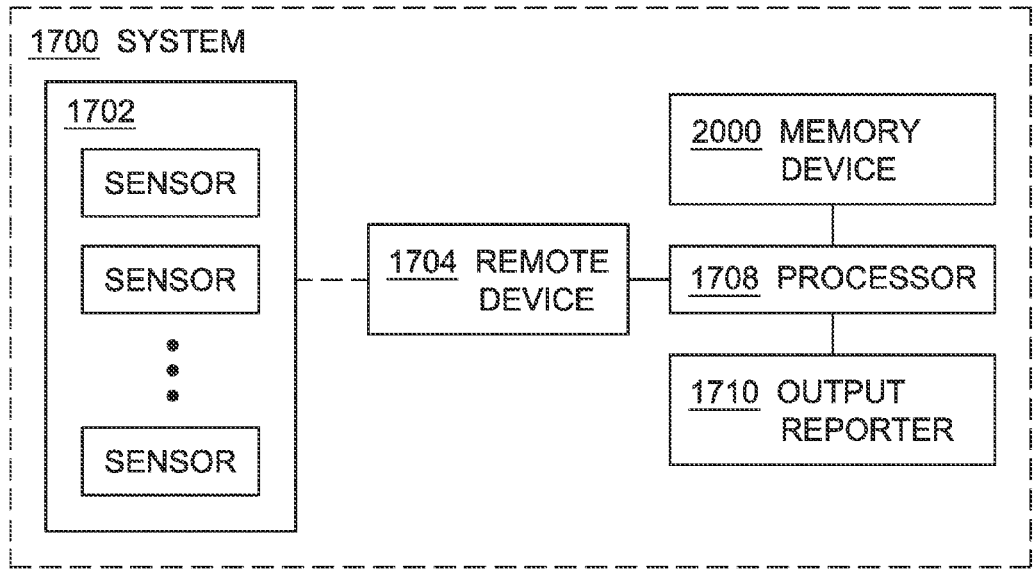
FIG. 20 is a schematic of an embodiment of a system such as shown in FIG. 17.

In embodiments (such as shown in FIG. 20), the system 1700 includes a memory device 2000 configured to store data associated with operation of the system 1700, such as data associated with interactions between the human appendage 114 and one or more environmental objects 300 (e.g., where such interactions can be derived from the one or more output signals from the plurality of sensors 1702). In embodiments, the memory device 2000 can correspond to one or more of the memory device 500 or the memory device 1200 described herein, including but not limited to the structural and functional characteristics thereof. For example, the memory device 2000 can include, but is not limited to, a computer memory device, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other medium which can be used to store the desired information maintained by the system 1700 and which can be accessed by the processor 1708, the output reporter 1710, or other associated accessing device. In embodiments, the memory device 2000 can store data associated with an impact or near impact between the human appendage 114 and the respective environmental object 300. The data associated with an impact between the human appendage 114 and the respective environmental object 300 can include, but is not limited to, a time of the impact between the human appendage 114 and the respective environmental object 300, a location of impact between the human appendage 114 and the respective environmental object 300, or a frequency of occurrences of impact between the human appendage 114 and the respective environmental object 300. In embodiments, the memory device 2000 can store data associated with when the distance between the human appendage 114 and the respective environmental object 300 is less than the threshold distance. The data associated with when the distance between the human appendage 114 and the respective environmental object 300 is less than the threshold distance can include, but is not limited to, data associated with a time of when the distance between the human appendage 114 and the respective environmental object 300 is less than the threshold distance, a location corresponding to where the distance between the human appendage 114 and the respective environmental object 300 became less than the threshold distance, or a frequency of instances of when the distance between the human appendage 114 and the respective environmental object 300 is less than the threshold distance.

Figure 21:
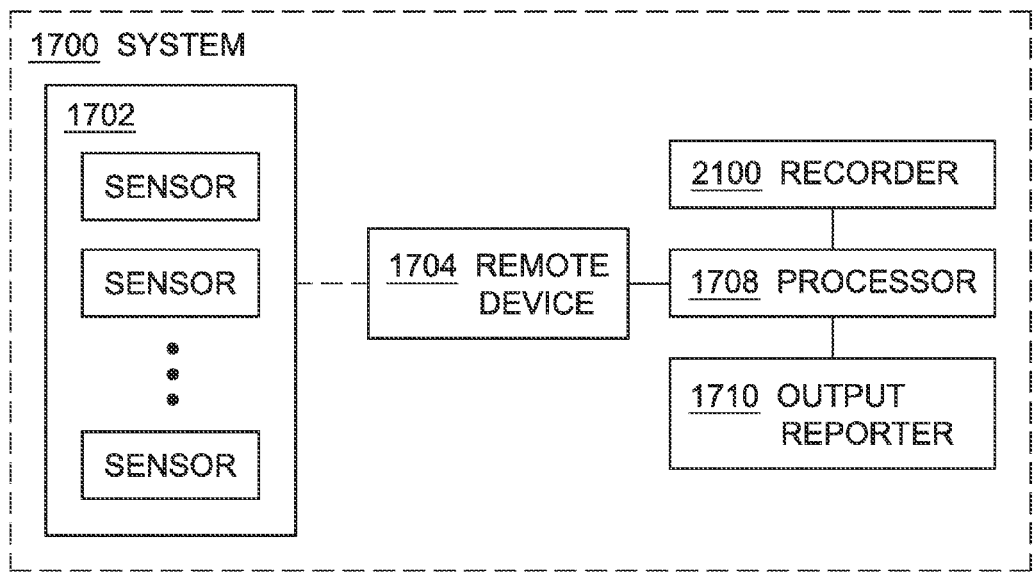
FIG. 21 is a schematic of an embodiment of a system such as shown in FIG. 17.

In embodiments (such as shown in FIG. 21), the system 1700 can include a recorder 2100 operably coupled to the processor 1708. In general, the recorder 2100 is configured to record, store, or the like, data, output signals, and communication signals generated by one or more components of the system 1700. For example, the recorder 2100 can be configured to record the one or more output signals from the plurality of sensors 1702 in a memory device, such as the memory device 2000. In embodiments, the recorder 2100 is configured to store in the memory device 2000 data associated with an impact between the human appendage 114 and the respective environmental object 300. Such data can include, but is not limited to, a time of impact, a location of impact, or a frequency of impact. In embodiments, the recorder 2100 is configured to store in the memory device 2000 data associated with when the distance between the human appendage 114 and the respective environmental object 300 is less than the threshold distance. Such data can include, but is not limited to, a time corresponding to when the distance between the human appendage 114 and the respective environmental object 300 is less than the threshold distance, a location corresponding to when the distance between the human appendage 114 and the respective environmental object 300 is less than the threshold distance, or a frequency of instances of when the distance between the human appendage 114 and the respective environmental object 300 is less than the threshold distance.

In embodiments, the processor 1708 can be configured to make determinations regarding one or more physical aspects associated with at least one of the human appendage 114 and the respective environmental object 300. For example, the processor 1708 can be configured to determine a force of an impact between the human appendage 114 and the respective environmental object 300. The processor 1708 can access data from one or more sensors of the system 1700 to make such determinations. For example, the processor 1708 can access data from a force sensor, from a pressure sensor, from an accelerometer, or the like. In embodiments, the processor 1708 is configured to determine what a force of a potential impact would be, should such potential impact actually occur. For example, the processor 1708 can determine, based on at least a current or previous velocity, speed, or the like of the human appendage 114, what force the human appendage 114 would impact the respective environmental object 300 should the human appendage 114 and the respective environmental object 300 actually collide. In embodiments, the processor 1708 can extrapolate and/or interpolate one or more of positional data, speed data, velocity data, or acceleration data to estimate or predict the force at which the human appendage 114 and the respective environmental object 300 would collide.

The output reporter 1710 is configured to generate one or more communication signals to report information associated with operation of the system 1700. In embodiments, the output reporter 1710 is configured to generate one or more communication signals responsive to instruction by the processor 1708. In embodiments, the output reporter 1710 can correspond to one or more of the output reporter 110 or the output reporter 1010 described herein, including but not limited to the structural and functional characteristics thereof. For example, the information from the output reporter 1710 may be provided one or more of visually (e.g., via transmission or display of visual information), audibly (e.g., via transmission or display of auditory information), tactually (e.g., via presentation of tactile information), or as data (e.g., via transmission or display of one or more data signals associated with the information to convey). The output reporter 1710 can function in combination with the processor 1708 to provide visual, auditory, or tactile information associated with the human appendage 114 and/or the respective environmental object 300, such as the proximity of the human appendage 114 with respect to the respective environmental object 300, impact information, threshold information, or the like.

In embodiments, the output reporter 1710 generates (e.g., via the display device 900) a graphical representation of data associated with operation of the system 1700. The graphical representation can include a map-based display of the information, which can provide the data with respect to absolute or relative locations. The map can correspond to a region proximate one or more environmental objects 300 and can display information associated with interaction between the human appendage 114 and the one or more environmental objects 300. For example, the map can indicate frequency of impact (or near impact) between the human appendage 114 and various environmental objects 300 where the data is color-coded to differentiate between differing frequencies. Other presentations of data are possible, including but not limited to, topographical plots, bar plots, pie plots, or the like. As another example, the map can indicate time of impact (or near impact) between the human appendage 114 and various environmental objects 300 where the data is coded to differentiate between differing times of impact (or near impact).

In embodiments, the processor 1708 is configured to generate a recommendation based on one or more output signals from one or more of the remote device 1704 and the plurality of sensors 1702. The recommendation can include, but is not limited to, a recommendation pertaining to the respective environmental object 300, where such recommendation can reduce at least one of a likelihood of impact with the respective environmental object 300 or a degree of severity of impact with the respective environmental object 300. For example, in embodiments, the recommendation includes a recommendation to reposition the respective environmental object 300 to a new location within the environment. The new location within the environment can be a location that an individual is less likely to impact with the respective environmental object 300 as compared to the previous location (i.e., the location prior to the recommendation to reposition the respective environmental object 300). For example, the processor 1708 can access (e.g., from the memory device 2000) one or more modules configured to analyze the positioning of the respective environmental object 300 based on one or more output signals from one or more of the remote device 1704 and the plurality of sensors 1702. Where the processor 1708 determines that the current position of the respective environmental object 300 results in too many impacts (e.g., the number of impacts between the human appendage 114 and the respective environmental object 300 exceeds a threshold impact value), the processor 1708 can generate the recommendation to reposition the respective environmental object 300 to a new location within the environment. The new location within the environment can include one or more of a different location within the environment than the previous position prior to the recommendation to reposition the respective environmental object 300, a location within a threshold distance from the previous position, a location outside of a threshold distance from the previous position, a location determined to have a probability of fewer impacts between the human appendage 114 and the respective environmental object 300, or so forth. In embodiments, the processor 1708 conveys the recommendation to reposition the respective environmental object 300 via the output reporter 1710. For example, the output reporter 1710 can generate one or more of a visual indication of the recommendation (e.g., via the display device 900), an audible indication of the recommendation (e.g., via the audio device 902), a tactile indication of the recommendation (e.g., via the tactile device 904), a physical indication of the recommendation (e.g., via the printing device 906), or a transmitted indication via one or more data signals (e.g., via the transmitter 908).

In embodiments, the processor 1708 is configured to generate a visible recommendation associated with a map corresponding to a region proximate the respective environmental object 300. The processor 1708 can generate the map via the output reporter 1710 to provide the visible recommendation. The map can include information including but not limited to, a recommended location to reposition the respective environmental object 300, a listing of areas proximate the respective environmental object 300 within the environment to which the respective environmental object 300 can be repositioned, a region proximate the respective environmental object 300 within a threshold distance, a region corresponding to locations outside of a threshold distance from the respective environmental object 300, data associated with impact frequency associated with one or more environmental objects, or so forth. For example, in embodiments, the processor 1708 generates the map via the output reporter 1710, wherein the map provides a visual distinction between varying intensities of impact between respective environmental objects (e.g., lower wavelength colors for areas corresponding to more impacts, higher wavelength colors for areas corresponding to fewer impacts, etc.).

In embodiments, the recommendation generated by the processor 1708 includes a recommendation to provide the respective environmental object 300 with a cushioning material. The cushioning material can reduce a degree of severity of impact with the respective environmental object 300 by absorbing or mitigating at least a portion of the force of impact between the human appendage 114 and the respective environmental object 300. For example, cushioning material can include, but is not limited to, fibrous materials (e.g., synthetic fibers, fabric, felt, paper, cardboard, feather, etc.), polymeric materials (e.g., foam, memory foam, rubber, polystyrene, polypropylene, polyethylene, polyurethane, etc.), entrapped gas material (e.g., air cushions, gas enclosed within plastic film, etc.), mechanical devices (e.g., shock absorber, spring-based device, pneumatic device, etc.), or the like. The processor 1708 can access (e.g., from the memory device 2000) one or more modules configured to analyze force of impacts between the respective environmental object 300 and another object (e.g., the human appendage 114) based on one or more output signals from one or more of the remote device 1704 or the plurality of sensors 1702. In embodiments, when the processor 1708 determines that one or more impacts with the environmental object 300 results in a force of impact that exceeds a threshold force of impact value, the processor 1708 can generate the recommendation to provide the respective environmental object 300 with a cushioning material to reduce or mitigate the force of subsequent impacts with the respective environmental object 300. In embodiments, the processor 1708 conveys the recommendation to provide the cushioning material to the respective environmental object 300 via the output reporter 1710. For example, the output reporter 1710 can generate one or more of a visual indication of the recommendation (e.g., via the display device 900), an audible indication of the recommendation (e.g., via the audio device 902), a tactile indication of the recommendation (e.g., via the tactile device 904), a physical indication of the recommendation (e.g., via the printing device 906), or a transmitted indication via one or more data signals (e.g., via the transmitter 908).

In embodiments, the recommendation generated by the processor 1708 includes a recommendation to provide the respective environmental object 300 with a visible indicator. The visible indicator can reduce the likelihood of impact between the human appendage 114 and the respective environmental object 300 by providing a visual indication associated with the position of the respective environmental object 300 within the environment. For example, the visual indicator can include a visible light source that can be placed on/near the respective environmental object 300 to provide an individual with a visual indication associated with the position of the respective environmental object 300 within the environment. The visible light source can illuminate at least a portion of the respective environmental object 300, which can assist an individual in viewing the respective environmental object 300, such as during periods of darkness within the environment (e.g., nighttime, power failure, etc.). In embodiments, the processor 1708 is configured to activate the visual indicator based upon one or more output signals from one or more of the remote device 1704 or the plurality of sensors 1702. For example, the output signals from one or more of the remote device 1704 or the plurality of sensors 1702 can provide an indication that the human appendage 114 is within a threshold distance from the respective environmental object, whereby the processor 1708 activates the visual indicator to provide a warning to the individual regarding a potential impact with the respective environmental object 300.

In embodiments, the recommendation generated by the processor 1708 includes a recommendation to provide the respective environmental object 300 with an audible indicator. The audible indicator can reduce the likelihood of impact between the human appendage 114 and the respective environmental object 300 by providing an auditory indication associated with the position of the respective environmental object 300 within the environment. For example, the audible indicator can include an alarm device or speaker device that can be placed on/near the respective environmental object 300 to provide an individual with an auditory indication associated with the position of the respective environmental object 300 within the environment. The audible indicator can alert an individual to the presence of the respective environmental object 300, which can assist an individual in avoiding contact or impact with the respective environmental object 300, such as during periods of darkness within the environment (e.g., nighttime, power failure, etc.), for individuals with visual impairments, or the like. In embodiments, the processor 1708 is configured to activate the audible indicator based upon one or more output signals from one or more of the remote device 1704 or the plurality of sensors 1702. For example, the output signals from one or more of the remote device 1704 or the plurality of sensors 1702 can provide an indication that the human appendage 114 is within a threshold distance from the respective environmental object 300, whereby the processor 1708 activates the audible indicator to provide a warning to the individual regarding a potential impact with the respective environmental object 300.

In embodiments, the output reporter 1710 is configured to generate an alert responsive to instruction by the processor 1708 when a distance between the human appendage 114 and the respective environmental object 300 is less than a threshold distance. The respective environmental object 300 can be identified by the system 1700 as at least one of a risk for impact with the human appendage 114 or a previously impacted object (e.g., previously impact by the human appendage 114, another environmental object, etc.). For example, the processor 1708 can access (e.g., from the memory device 2000) one or more modules configured to analyze a position of a particular environmental object 300 (or an analog for the environmental object, such as a sensor of the plurality of sensors 1702, etc.) relative to the human appendage 114 based at least in part on one or more output signals from one or more of the remote device 1704 or the plurality of sensors 1702 to determine a distance between the human appendage 114 and the respective environmental object 300. The processor 1708 can then compare the determined distance between the human appendage 114 and the respective environmental object 300 to a threshold distance to determine whether the determined distance is less than the threshold distance. The threshold distance can be a stored value that can depend on spacing considerations (e.g., constraints of the size of the environment), can depend on particular environmental objects (e.g., more dangerous environmental objects can have a larger attributed threshold distance), or the like. Such comparison can occur on a periodic basis, a continuous basis, or the like. Where the processor 1708 determines that the distance between the respective environmental object 300 and the human appendage 114 is less than the threshold distance, the processor 1708 can instruct the output reporter 1710 to generate an alert. In embodiments, the alert can be one or more of an audible alert, a visual alert, or a tactile alert.

In embodiments, the alert is associated with the human appendage 114. An alert associated with the human appendage 114 can include, but is not limited to, one or more of an alert displayed on the human appendage 114, an alert projected to the human appendage 114 (e.g., from a location remote from the human appendage 114), an alert indicating the human appendage 114, or the like. For example, the alert can include, but is not limited to, an alert originating from a device on the human appendage 114, an alert indicating or identifying the human appendage 114 (e.g., displaying the alert on a screen that provides at least an indication of the human appendage 114, such as by accentuating an area, region, object, etc. on a map), a visual or audible alert projected from a device onto the human appendage 114 (e.g., directing light or sound at the human appendage 114), or the like. In embodiments, the alert is associated with the respective environmental object 300. An alert associated with the respective environmental object 300 can include, but is not limited to, one or more of an alert displayed on the respective environmental object 300, an alert projected to the respective environmental object 300 (e.g., from a location remote from the respective environmental object 300), an alert indicating the respective environmental object 300, or the like. For example, the alert can include, but is not limited to, an alert originating from a device on the respective environmental object 300, an alert indicating or identifying the respective environmental object 300 (e.g., displaying the alert on a screen that provides at least an indication of the respective environmental object 300, such as by accentuating an area, region, object, etc. on a map), a visual or audible alert projected from a device onto respective environmental object 300 (e.g., directing light or sound at the respective environmental object 300), or the like.

Figure 22:
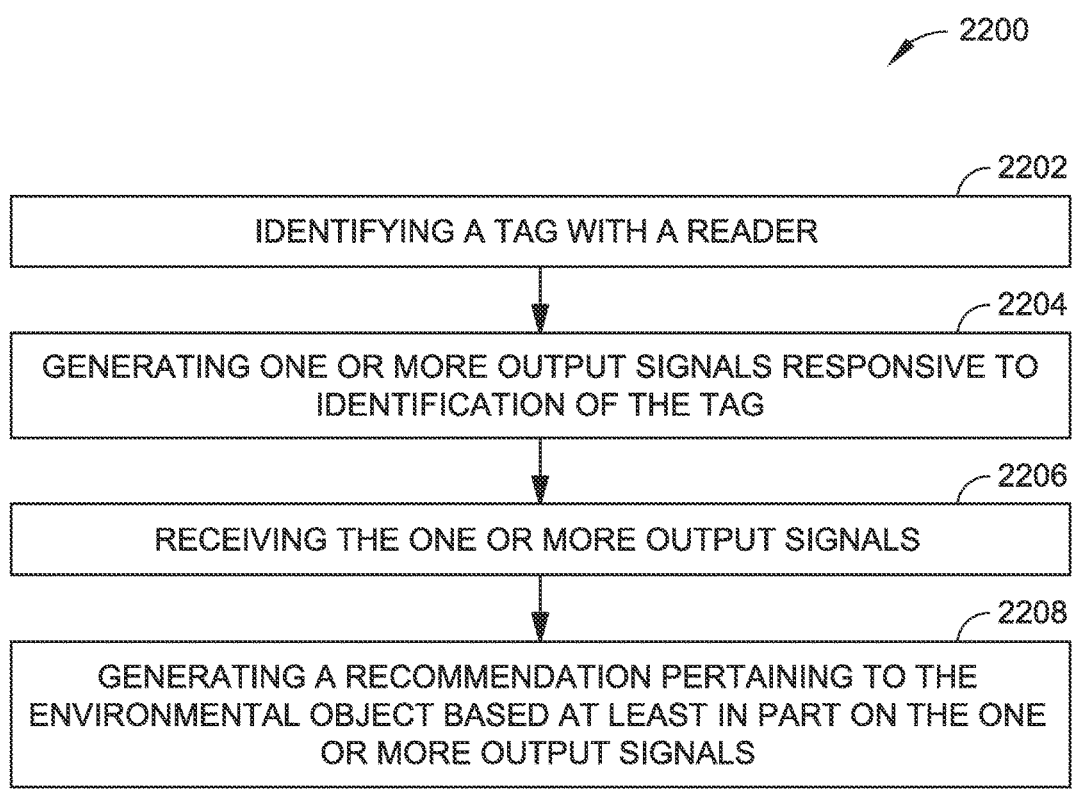
FIG. 22 is a flowchart of a method of monitoring one or more of a human appendage and an environmental object within an environment.

FIG. 22 illustrates a method 2200 for monitoring one or more of a human appendage and an environmental object within an environment, which can result in generating recommendations pertaining to the environmental object to avoid or reduce impact between the human appendage and the environmental object. Method 2200 shows identifying a tag with a reader in block 2202, where the reader and the tag are paired, each of which is configured for individual positioning proximate a human appendage and an environmental object. For example, the reader 104 of the tag and reader pair 112 can identify the tag 102. Method 2200 also includes generating one or more output signals responsive to identification of the tag in block 2204. For example, the reader 104 can generate one or more output signals responsive to identification of the tag 102, where the one or more output signals can correspond to a threshold associated with one or more of the tag 102 or the reader 104. Method 2200 also includes receiving the one or more output signals in block 2206. For example, the processor 108 can receive the one or more output signals from the reader 104 of the tag and reader pair 112. Method 2200 further includes generating a recommendation pertaining to the environmental object based at least in part on the one or more output signals in block 2208, where the recommendation is directed to reducing at least one of a likelihood of impact with the environmental object or a degree of severity of impact with the environmental object. For example, the processor 108 can generate a recommendation pertaining to the environmental object 300 based at least in part on the one or more output signals from the reader 104. The recommendation can include, but is not limited to, a recommendation to reposition the environmental object 300, a recommendation to provide the environmental object 300 with a cushioning material, a recommendation to provide the environmental object 300 with a visible indicator, a recommendation to provide the environmental object 300 with an audible indicator, or the like.

Figure 23:
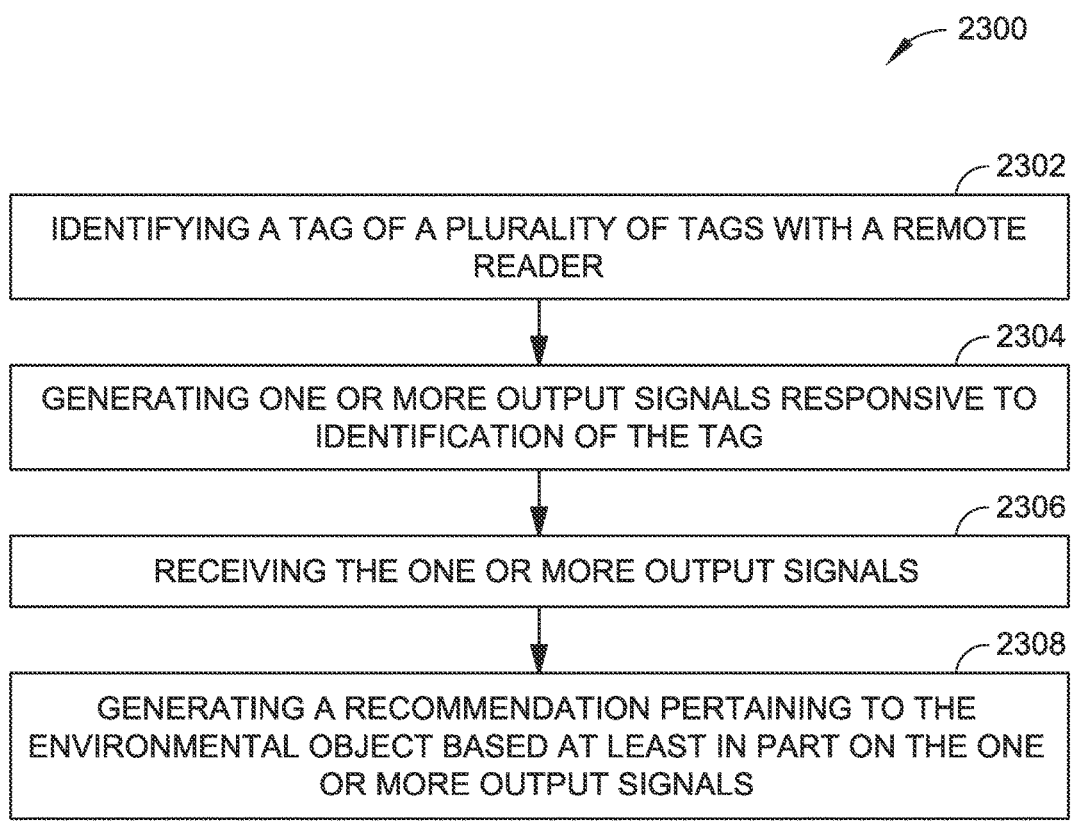
FIG. 23 is a flowchart of a method of monitoring one or more of a human appendage and an environmental object within an environment.

FIG. 23 illustrates a method 2300 for monitoring one or more of a human appendage and an environmental object within an environment, which can result in generating recommendations pertaining to the environmental object to avoid or reduce impact between the human appendage and the environmental object. Method 2300 shows identifying a tag of a plurality of tags with a remote reader in block 2302, where at least one tag positioned on a human appendage and at least one tag positioned on an environmental object. For example, the remote reader 1004 can distinctly identify a tag of the plurality of tags 1002, where at least one tag is positioned on the human appendage 114 and at least one tag is positioned on the environmental object 300. Method 2300 also includes generating one or more output signals responsive to identification of the tag in block 2304. For example, the remote reader 1004 can generate one or more output signals responsive to identification of the tag of the plurality of tags 1002, where the one or more output signals can correspond to a threshold associated with the tag positioned on the human appendage 114 and the tag positioned on the environmental object 300. Method 2300 also includes receiving the one or more output signals in block 2306. For example, the processor 1008 can receive the one or more output signals from the remote reader 1004. Method 2300 further includes generating a recommendation pertaining to the environmental object based at least in part on the one or more output signals in block 2308, where the recommendation is directed to reducing at least one of a likelihood of impact with the environmental object or a degree of severity of impact with the environmental object. For example, the processor 1008 can generate a recommendation pertaining to the environmental object 300 based at least in part on the one or more output signals from the remote reader 1004. The recommendation can include, but is not limited to, a recommendation to reposition the environmental object 300, a recommendation to provide the environmental object 300 with a cushioning material, a recommendation to provide the environmental object 300 with a visible indicator, a recommendation to provide the environmental object 300 with an audible indicator, or the like.

Figure 24:
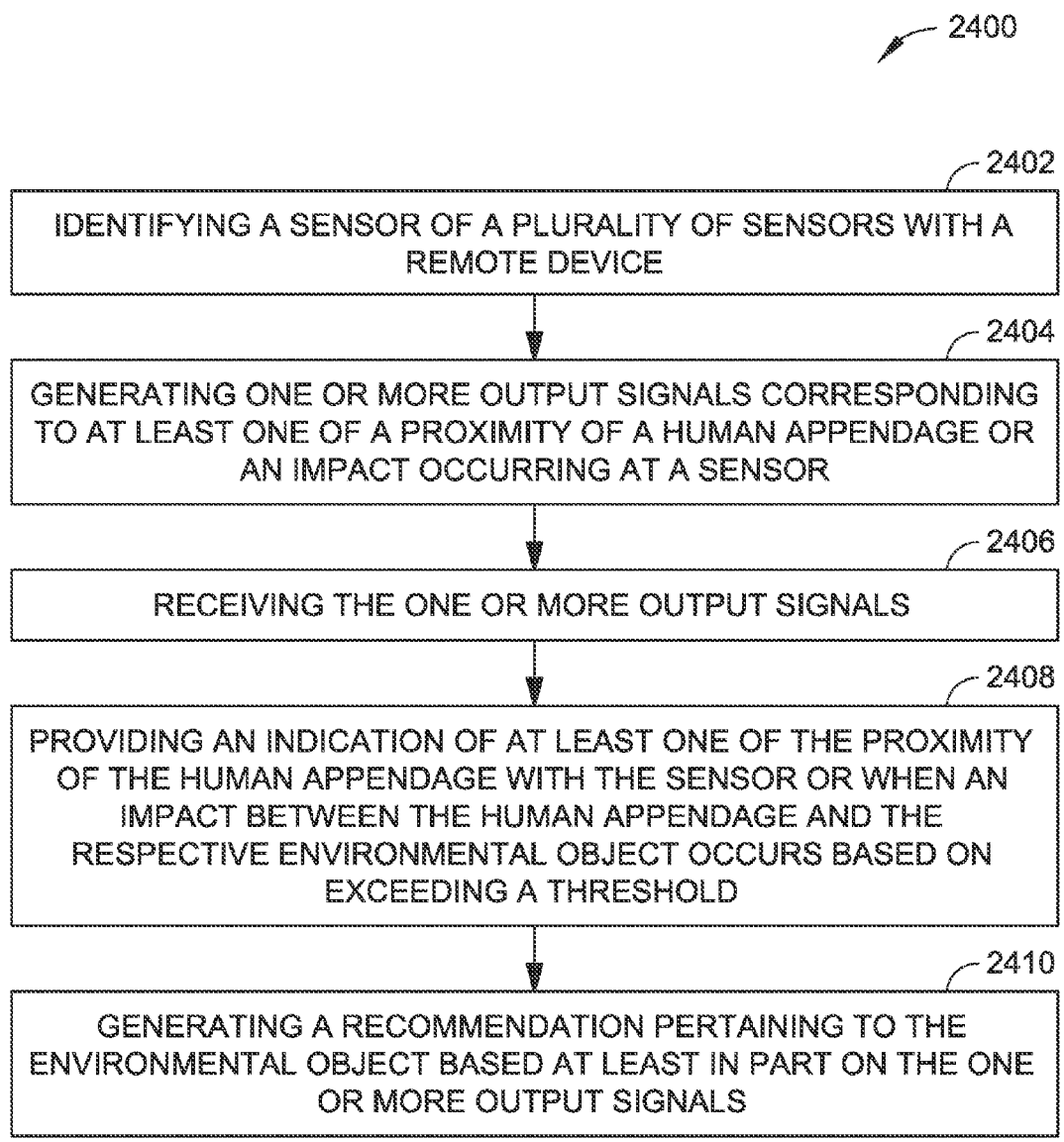
FIG. 24 is a flowchart of a method of monitoring one or more environmental objects within an environment.

FIG. 24 illustrates a method 2400 for monitoring one or more of a human appendage and an environmental object within an environment, which can result in generating recommendations pertaining to the environmental object to avoid or reduce impact between the human appendage and the environmental object. Method 2400 shows identifying a sensor of a plurality of sensors with a remote device in block 2402, where each sensor is configured for positioning proximate a respective environmental object of a plurality of environmental objects. For example, the remote device 1704 can distinctly identify a sensor of the plurality of sensors 1702, where a first sensor 1702a is positioned on a first environmental object 300a and a second sensor 1702b is positioned on a second environmental object 300b. Method 2400 also includes generating one or more output signals corresponding to at least one of a proximity of a human appendage or an impact occurring at a sensor in block 2404. For example, each sensor of the plurality of sensors 1702 can be configured to generate one or more output signals corresponding to at least one of a proximity of the human appendage 114 with the respective sensors or an impact between the human appendage 114 and the respective environmental object 300 on which the sensor is located. Method 2400 also includes receiving the one or more output signals in block 2406. For example, the remote device 1704 can receive the one or more output signals from the sensors of the plurality of sensors 1702, where the remote device 1704 can be coupled to the processor 1708 for processing of the one or more output signals. Method 2400 also includes providing an indication of at least one of the proximity of the human appendage with the sensor or when an impact between the human appendage and the respective environmental object occurs based on exceeding a threshold in block 2408. For example, the processor 1708 can process the one or more output signals to provide an indication of at least one of the proximity of the human appendage with the sensor of the plurality of sensors 1702 or when an impact between the human appendage 114 and the environmental object 300 occurs based on a threshold value (e.g., distance threshold, frequency threshold, etc.) being exceeded. Method 2400 further includes generating a recommendation pertaining to the environmental object based at least in part on the one or more output signals in block 2410, where the recommendation is directed to reducing at least one of a likelihood of impact with the environmental object or a degree of severity of impact with the environmental object. For example, the processor 1708 can generate a recommendation pertaining to the environmental object 300 based at least in part on the one or more output signals from the plurality of sensors 1702. The recommendation can include, but is not limited to, a recommendation to reposition the environmental object 300, a recommendation to provide the environmental object 300 with a cushioning material, a recommendation to provide the environmental object 300 with a visible indicator, a recommendation to provide the environmental object 300 with an audible indicator, or the like.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations can include software or other control structures. Electronic circuitry, for example, may have one or more paths of electrical current constructed and arranged to implement various functions as described herein. In some implementations, one or more media can be configured to bear a device-detectable implementation when such media hold or transmit device detectable instructions operable to perform as described herein. In some variants, for example, implementations can include an update or modification of existing software or firmware, or of gate arrays or programmable hardware, such as by performing a reception of or a transmission of one or more instructions in relation to one or more operations described herein. Alternatively or additionally, in some variants, an implementation can include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications.

The foregoing detailed description has set forth various embodiments of the devices and/or processes via the use of block diagrams, flowcharts, and/or examples. Insofar as such block diagrams, flowcharts, and/or examples contain one or more functions and/or operations, each function and/or operation within such block diagrams, flowcharts, or examples can be implemented, individually and/or collectively, by a wide range of hardware, software, firmware, or virtually any combination thereof. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, the various embodiments described herein can be implemented, individually and/or collectively, by various types of electro-mechanical systems having a wide range of electrical components such as hardware, software, firmware, and/or virtually any combination thereof and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Examples of electro-mechanical systems include but are not limited to a variety of consumer electronics systems, medical devices, as well as other systems such as motorized transport systems, factory automation systems, security systems, and/or communication/computing systems. Electro-mechanical as used herein is not necessarily limited to a system that has both electrical and mechanical actuation except as context may dictate otherwise.

In a general sense, the various aspects described herein can be implemented, individually and/or collectively, by a wide range of hardware, software, firmware, and/or any combination thereof and can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein can be implemented in an analog or digital fashion or some combination thereof.

With respect to the use of substantially any plural and/or singular terms herein, the plural can be translated to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "operably coupled to" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). Typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

This disclosure has been made with reference to various example embodiments. However, those skilled in the art will recognize that changes and modifications may be made to the embodiments without departing from the scope of the present disclosure. For example, various operational steps, as well as components for carrying out operational steps, may be implemented in alternate ways depending upon the particular application or in consideration of any number of cost functions associated with the operation of the system; e.g., one or more of the steps may be deleted, modified, or combined with other steps.

Additionally, as will be appreciated by one of ordinary skill in the art, principles of the present disclosure, including components, may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create a means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof are intended to cover a non-exclusive inclusion, such that a process, a method, an article, or an apparatus that comprises a list of elements does not include only those elements but may include other elements not expressly listed or inherent to such process, method, system, article, or apparatus.

In embodiments, the system is integrated in such a manner that the system operates as a unique system configured specifically for function of one or more of the systems described herein (e.g., system 100, system 1000, system 1700, etc.) used to monitor an environment and the environmental object(s) therein, and any associated computing devices of the system operate as specific use computers for purposes of the claimed system, and not general use computers. In embodiments, at least one associated computing device of the system operates as a specific use computer for purposes of the claimed system, and not a general use computer. In embodiments, at least one of the associated computing devices of the system is hardwired with a specific ROM to instruct the at least one computing device. In embodiments, one of skill in the art recognizes that the systems described herein (e.g., system 100, system 1000, system 1700, etc.) and associated systems/devices effect an improvement at least in the technological field of environmental sensing.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A system, comprising:
a tag and a reader pair, the tag and the reader configured for individual positioning proximate a human appendage and an environmental object, wherein the reader is configured to identify the tag;
a substrate configured to conform to the human appendage, the substrate coupled to at least one of the tag or the reader, the other of the tag or the reader configured to be coupled to the environmental object;
a processor operably coupled to the reader and configured to receive one or more output signals from the reader, the one or more output signals corresponding to a threshold associated with the tag or the reader, the processor being configured to generate a recommendation pertaining to the environmental object to reduce at least one of a potential for impact with the environmental object or a degree of severity of impact with the environmental object; and
an output reporter operably coupled to the processor and configured to generate one or more communication signals responsive to instruction by the processor.

2. The system of claim 1, wherein the processor is configured to determine that an impact has occurred between the human appendage and the environmental object based on the one or more output signals from the reader.

3. The system of claim 1, wherein the processor is configured to determine that a distance between the human appendage and the environmental object is less than a threshold distance based on the one or more output signals from the reader.

4. The system of claim 1, further including:
an impact sensor associated with one or more of the tag and the reader, the processor configured to receive one or more output signals from the impact sensor.

5. The system of claim 4, wherein the processor is configured to determine that an impact has occurred between the human appendage and the environmental object based at least in part on the one or more output signals from the impact sensor.

6. The system of claim 4, wherein the processor is configured to determine when a distance between the human appendage and the environmental object is less than a threshold distance based at least in part on the one or more output signals from the impact sensor.

7. The system of claim 1, further including:
a location sensor configured to generate one or more output signals associated with a location of at least one of the human appendage and the environmental object, the processor configured to receive the one or more output signals from the location sensor.

8. The system of claim 7, wherein the processor is configured to determine that an impact has occurred between the human appendage and the environmental object based at least in part on the one or more output signals from the location sensor.

9. The system of claim 7, wherein the processor is configured to determine when a distance between the human appendage and the environmental object is less than a threshold distance based at least in part on the one or more output signals from the location sensor.

10. The system of claim 7, wherein the reader includes the location sensor configured to measure the location of at least one of the reader or the tag.

11. The system of claim 10, wherein the location sensor includes at least one accelerometer, wherein the location sensor is configured to measure at least one of a distance or direction from an initiation point based on activation of the accelerometer.

12. The system of claim 1, further including:
a recorder operably coupled to the processor and configured to record the one or more output signals in a memory device.

13. The system of claim 1, wherein the processor is configured to generate a visible recommendation associated with a map corresponding to a region proximate the environmental object.

14. The system of claim 1, wherein the recommendation includes a recommendation to reposition the environmental object.

15. The system of claim 1, wherein the output reporter is configured to generate an alert responsive to instruction by the processor when a distance between the human appendage and the environmental object is less than a threshold distance, wherein the environmental object is identified as at least one of a risk for impact with the human appendage or a previously impacted object.

16. The system of claim 1, wherein the tag includes at least one of an RFID tag, a magnetic material, a metallic material, or an optical label, and wherein the reader includes at least one of an RFID reader, a magnetic detector, a magnet configured to detect the metallic material, or an optical reader.

17. The system of claim 1, wherein the output reporter includes at least one of a display device configured to provide a visual representation of the one or more output signals, an audio device configured to provide an auditory representation of the one or more output signals, a tactile device configured to provide a tactile representation of the one or more output signals, and a printing device.

18. The system of claim 17, wherein the output reporter includes the display device, wherein the visual representation includes a map corresponding to a region proximate the environmental object.

19. The system of claim 1, wherein the recommendation includes a recommendation to provide the environmental object with at least one of a cushioning material, a visible indicator, and an audible indicator.

* * * * *